US010145772B2

(12) United States Patent
Troxler et al.

(10) Patent No.: US 10,145,772 B2
(45) Date of Patent: *Dec. 4, 2018

(54) MATERIAL PROPERTY GAUGES AND METHODS FOR DETERMINING A PROPERTY OF A MATERIAL

(71) Applicant: Troxler Electronic Laboratories, Inc., Research Triangle Park, NC (US)

(72) Inventors: Robert Ernest Troxler, Raleigh, NC (US); Wewage Hiran Linus Dep, Chapel Hill, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,659

(22) Filed: Jun. 22, 2016

(65) Prior Publication Data

US 2016/0305861 A1 Oct. 20, 2016
US 2017/0363527 A9 Dec. 21, 2017

Related U.S. Application Data

(63) Continuation of application No. 14/794,927, filed on Jul. 9, 2015, now Pat. No. 9,400,240, which is a
(Continued)

(51) Int. Cl.
*G01N 23/02* (2006.01)
*G01N 33/24* (2006.01)
*G01N 9/24* (2006.01)
*G01N 19/10* (2006.01)
*G01N 23/06* (2018.01)
(Continued)

(52) U.S. Cl.
CPC .............. *G01N 9/24* (2013.01); *G01N 19/10* (2013.01); *G01N 23/005* (2013.01); *G01N 23/06* (2013.01);
(Continued)

(58) Field of Classification Search
CPC ........ G01N 23/02; G01N 23/08; G01N 33/28; G01N 33/42
See application file for complete search history.

(56) References Cited

U.S. PATENT DOCUMENTS 4,442,701 A    4/1984  Cowherd et al.
4,766,319 A    8/1988  Regimand
(Continued)

OTHER PUBLICATIONS

TROXLER Electronic Laboratories, Inc., Mar. 2004, "Model 3451 Enhanced RoadReader™ Plus Surface Moisture-Density Gauge, Manual of Operation and Instruction", Edition 1.0., pp. 1-2, 2-1 to 2-22.*
(Continued)

*Primary Examiner* — Mark R Gaworecki
(74) *Attorney, Agent, or Firm* — Olive Law Group, PLLC

(57) ABSTRACT

The subject matter described herein includes methods, systems, and computer program products for measuring the density of a material. According to one aspect, a material property gauge includes a nuclear density gauge for measuring the density of a material. A radiation source adapted to emit radiation into a material and a radiation detector operable to produce a signal representing the detected radiation. A first material property calculation function may calculate a value associated with the density of the material based upon the signal produced by the radiation detector. The material property gauge includes an electromagnetic moisture property gauge that determines a moisture property of the material. An electromagnetic field generator may generate an electromagnetic field where the electromagnetic field sweeps through one or more frequencies and penetrates into the material. An electromagnetic sensor may determine a frequency response of the material to the electromagnetic field across the several frequencies.

45 Claims, 14 Drawing Sheets

Related U.S. Application Data continuation of application No. 14/181,865, filed on Feb. 17, 2014, now Pat. No. 9,091,627, which is a continuation of application No. 13/794,049, filed on Mar. 11, 2013, now Pat. No. 8,692,184, which is a continuation of application No. 13/644,394, filed on Oct. 4, 2012, now Pat. No. 8,492,706, which is a continuation of application No. 13/310,790, filed on Dec. 4, 2011, now Pat. No. 8,294,084, which is a continuation of application No. 13/089,196, filed on Apr. 18, 2011, now Pat. No. 8,071,937, which is a continuation of application No. 12/910,745, filed on Oct. 22, 2010, now Pat. No. 7,928,360, which is a continuation of application No. 12/534,739, filed on Aug. 3, 2009, now Pat. No. 7,820,960, which is a continuation of application No. 11/512,732, filed on Aug. 30, 2006, now Pat. No. 7,569,810.

(60) Provisional application No. 60/719,071, filed on Sep. 21, 2005, provisional application No. 60/712,754, filed on Aug. 30, 2005.

(51) Int. Cl.
*G01N 23/203* (2006.01)
*G01N 23/00* (2006.01)
*G01N 27/04* (2006.01)

(52) U.S. Cl.
CPC ......... *G01N 23/203* (2013.01); *G01N 27/048* (2013.01); *G01N 2223/1013* (2013.01); *H05K 999/99* (2013.01)

(56) References Cited

U.S. PATENT DOCUMENTS

| 5,455,516 | A  * | 10/1995 | Jean ............... G01N 22/04 324/636 |
| 6,369,381 | B1   | 4/2002  | Troxler et al. |
| 6,414,497 | B1   | 7/2002  | Sovik et al. |
| 7,219,024 | B2   | 5/2007  | Gamache et al. |
| 7,376,530 | B2   | 5/2008  | Bienvenu et al. |
| 7,928,360 | B2 * | 4/2011  | Troxler ............ G01N 33/42 250/269.1 |
| 8,071,937 | B2 * | 12/2011 | Troxler ............ G01N 33/42 250/269.1 |
| 8,294,084 | B2 * | 10/2012 | Troxler ............ G01N 33/42 250/269.3 |
| 8,492,706 | B2 * | 7/2013  | Troxler ............ G01N 33/42 250/269.1 |
| 8,692,184 | B1 * | 4/2014  | Troxler ............ G01N 33/42 250/269.1 |
| 2004/0260504 | A1 * | 12/2004 | Bienvenu ............ E01C 19/00 702/127 |
| 2005/0150278 | A1   | 7/2005  | Troxler et al. |

OTHER PUBLICATIONS

TROXLER Electronic Laboratories, Inc., Mar. 2004, "Model 3451 Enhanced RoadReader™ Plus Surface Moisture-Density Guage, Manual of Operationa dn instruction", Edition 1.0., pp. 1-2, 2-1 to 2-2.

* cited by examiner

MATERIAL PROPERTY GAUGES AND METHODS FOR DETERMINING A PROPERTY OF A MATERIAL

CROSS REFERENCE TO RELATED APPLICATIONS

This application is a continuation of U.S. patent application Ser. No. 14/794,927 filed Jul. 9, 2015, which is a continuation of U.S. patent application Ser. No. 14/181,865 filed Feb. 17, 2014 (now U.S. Pat. No. 9,091,627), which is a continuation of U.S. patent application Ser. No. 13/794,049 filed Mar. 11, 2013 (now U.S. Pat. No. 8,692,184), which is a continuation of U.S. patent application Ser. No. 13/644,394 filed Oct. 4, 2012 (now U.S. Pat. No. 8,492,706), which is a continuation of U.S. patent application Ser. No. 13/310,790, filed Dec. 4, 2011 (now U.S. Pat. No. 8,294,084), which is a continuation of U.S. patent application Ser. No. 13/089,196, filed Apr. 18, 2011 (now U.S. Pat. No. 8,071,937), which is a continuation of U.S. patent application Ser. No. 12/910,745 filed Oct. 22, 2010 (now U.S. Pat. No. 7,928,360), which is a continuation of U.S. patent application Ser. No. 12/534,739 filed Aug. 3, 2009 (now U.S. Pat. No. 7,820,960), which is a continuation of U.S. patent application Ser. No. 11/512,732 filed Aug. 30, 2006 (now U.S. Pat. No. 7,569,810), which claims the benefit of U.S. Provisional Patent Application No. 60/712,754, filed Aug. 30, 2005, and U.S. Provisional Patent Application No. 60/719,071, filed Sep. 21, 2005, the disclosures of which are incorporated by reference herein in their entireties. The disclosure of U.S. patent application Ser. No. 11/513,334, filed Aug. 30, 2006 (now U.S. Pat. No. 7,581,446) is incorporated by reference in its entirety.

TECHNICAL FIELD

The subject matter described herein relates to measuring material properties. More particularly, the subject matter described herein relates to methods, systems, and computer program products for measuring the density of a material including a non-nuclear moisture property detector.

BACKGROUND

In construction engineering, some of the most important properties of interest are volumetric and mechanistic properties of a bulk soil mass. In particular, there are procedures in construction engineering practice that relate total volume $V_r$, mass of water $M_W$, and mass of dry solids $M_S$ to the performance of a structure built on a soils foundation. Thus, the measurements of these properties are important for construction engineering.

Material density and moisture content are other important material properties used for design, quality control, and quality assurance purposes in the construction industry. Some exemplary techniques for measuring the density and moisture content of soils include nuclear, sand cone, and drive cone, as described by the American Society of Testing and Materials (ASTM) standards D-2922, D-3017, and D-1556, and the American Association of State Highway and Transportation Officials (AASHTO) standards T-238, T-239, T-191, and T-204. The nuclear measurement technique is non-destructive and calculates both the density and the moisture content in a matter of minutes. The sand cone and drive cone measurement techniques require the moisture content test of ASTM standard D-2216, which involves a time consuming evaporation process. The moisture content test involves heating a sample to 110° C. for at least 24 hours.

For road construction, there is an optimum water or moisture content that allows for obtaining a maximum density. An exemplary density test is described in ASTM standard D-698, wherein a field sample is prepared with different water contents, and compacted with like energy efforts. Hence, each sample has different water content, but the same compaction effort. The densities are then measured gravimetrically in the laboratory. The moisture content with the highest density is deemed the optimum condition and selected as the field target. Summarily, the objective of material compaction is the improvement of material properties for engineering purposes. Some exemplary improvements include reduced settling, improved strength and stability, improved bearing capacity of sub grades, and controlling of undesirable volume changes such as swelling and shrinkage.

In the road paving and construction industry, portable nuclear density gauges are used for measuring the density of asphalt pavement and soils. Often, an asphalt paving material is applied on a new foundation of compacted soil and aggregate materials. The density and moisture content of the soil and aggregate materials should meet certain specifications. Therefore, nuclear gauges have been designed to measure the density of the asphalt pavement and soils.

Nuclear density gauges typically include a source of gamma radiation which directs gamma radiation into the sample material. A radiation detector may be located adjacent to the surface of the sample material for detecting radiation scattered back to the surface. From this detector reading, the density of the sample material can be determined.

These nuclear gauges are generally designed to operate either in a backscatter mode or in both a backscatter mode and a transmission mode. In gauges capable of transmission mode, the radiation source is vertically moveable from a backscatter position, where it resides within the gauge housing, to a series of transmission positions, where it is inserted into holes or bores in the sample material to selectable depths.

Nuclear gauges capable of measuring the density of sample materials have been developed by the assignee of the present subject matter. For example, nuclear gauges for measuring the density of sample materials are disclosed in U.S. Pat. Nos. 4,641,030; 4,701,868; and 6,310,936, all of which are incorporated herein by reference in their entirety. The gauges described in these patents use a Cesium-137 (Cs-137) source of gamma radiation for density measurements, and Americium Beryllium (AmBe) neutron sources for moisture measurements. Paving material may be exposed to the gamma radiation produced by the Cs-137 source. Gamma radiation is Compton scattered by the paving material and detected by Geiger-Mueller tubes positioned to form at least one geometrically differing source-to-detector relationships. The density of the paving material is calculated based upon the gamma radiation counts detected by the respective detectors.

One difficulty to the use of nuclear density gauge is the use of a radioactive source and the associated regulations imposed by the U.S. Nuclear Regulatory Commission (NRC). The requirements for meeting NRC regulations are largely dependent on the quantity of radioactive source material used in a gauge. Thus, it is desirable to provide a nuclear density gauge having a smaller quantity of radioactive source material in order to reduce the requirements of the NRC for use of the gauge.

Another difficulty with nuclear gauges is the time required for making a density measurement of material. Delays in obtaining density measurements of soils during construction may delay or otherwise disturb the construction process. Thus, it is desirable to provide a nuclear density gauge operable to provide faster density measurements.

Accordingly, in light of the above described difficulties and needs associated with nuclear density gauges, there exists a need for improved methods, systems, and computer program products for measuring the density of material.

SUMMARY

The subject matter described herein includes methods, systems, and computer program products for measuring the density of a material. According to one aspect, a material property gauge includes a nuclear density gauge for measuring the density of a material. The nuclear density gauge includes a radiation source adapted to emit radiation into a material and a radiation detector operable to produce a signal representing the detected radiation. A first material property calculation function is configured to calculate a value associated with the density of the material based upon the signal produced by the radiation detector. The material property gauge further includes an electromagnetic moisture property gauge configured to determine a moisture property of the material. The electromagnetic moisture property gauge includes an electromagnetic field generator configured to generate an electromagnetic field where the electromagnetic field sweeps through one or more frequencies and penetrates into the material. The material includes at least one of a pavement material, aggregate base material, concrete, and a soil material. An electromagnetic sensor is configured to determine a frequency response of the material to the electromagnetic field across the one or more frequencies. A second material property calculation function is configured to correlate the frequency response to a moisture property of the material and to calculate a value representing the moisture property. The material property gauge further includes a third material property calculation function configured to determine a material property of the material based on the value associated with the density of the material and the value representing the moisture property of the material. As used herein, the terms "sample construction material," "sample material," "construction material," and "material" refer to any suitable material used in a construction process. Exemplary sample construction materials include soil, asphalt, pavement, stone, sub-base material, sub-grade material, cement, agricultural soils, batch plants, concrete curing rate, concrete chloride inclusion, sodium chloride content, concrete delamination, water content, water-cement materials, alkali-silica, various soils, flexible asphalt, and any combination thereof.

The subject matter described herein may be implemented using a computer program product comprising computer executable instructions embodied in a non-transitory computer-readable medium. Exemplary non-transitory computer-readable media suitable for implementing the subject matter described herein include chip memory devices, disk memory devices, programmable logic devices, and application specific integrated circuits.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1A:
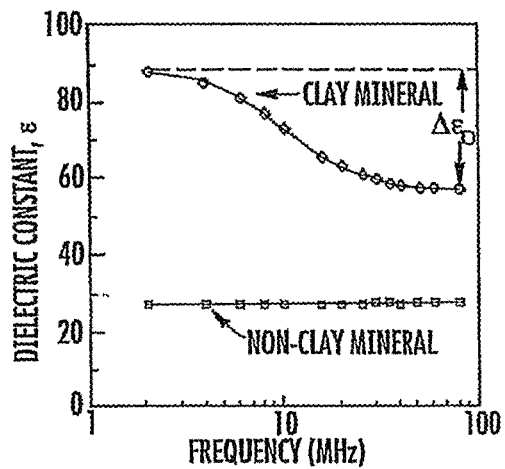
FIG. 1A is a graph of a comparison of dielectric constants of clay material and non-clay material over different frequencies.

The subject matter described herein includes methods, systems, and computer program products for measuring the density of a material and/or various other material properties. In one embodiment, the methods, systems, and computer program products described herein may determine the radiation propagation properties of a material under test for measuring the density of the material. According to one aspect, a nuclear density gauge may include a radiation source for positioning in an interior of a sample material, such as soil. The radiation source may emit radiation from the interior of the sample material for detection by a radiation detector. The radiation detector may produce a signal representing an energy level of detected radiation. The nuclear density gauge may also include a material property calculation function configured to calculate a value associated with the density of the sample material based upon the signals produced by the radiation detector.

In another embodiment, the methods, systems, and computer program products described herein may determine the radiation propagation and moisture properties of a material under test for measuring the density of the material. The material may be a construction related material such as soil or asphalt or concrete. In one aspect, a material property gauge may include a radiation source positioned for emitting radiation into a material under test. A radiation detector may detect radiation from the material and produce a signal representing the detected radiation. A moisture property detector may determine a moisture property of the material and produce a signal representing the moisture property. The material property gauge may include a material property calculation function configured to calculate a property value associated with the material based upon the signals produced by the radiation detector and the moisture property detector.

Initially, it is noted that there are two dominant interacting mechanisms with matter for gamma radiation with energies less than 1 mega electronvolt (MeV). For gamma ray energies less than 0.1 MeV, the dominant interaction is photoelectric absorption (PE) wherein the entire gamma radiation energy is provided for ejecting an electron from the atomic orbit. For common elements found in construction materials, the dominant interaction for gamma radiation energies greater than 0.2 MeV, is Compton scattering (CS), the scattering of photons by electrons in the atoms.

To explain the photon interaction types, consider a nuclear density gauge that includes a gamma radiation source for producing a parallel beam of photons with discrete energies having a uniform distribution. The beam of photons are directed through a sample material. If the photon interaction mechanism is essentially photoelectric absorption (depending on the reaction cross-section or probability, which is specific to the sample material), some of the photons are lost from the radiation beam due to absorption. Because of the absorption, the photon energy spectrum will vary from location to location in the sample material. Since cross sections are higher for low energy photons (i.e., energy less than 0.1 MeV), the low energy part of the spectrum shows a decreasing response or dip. The spectrum dip increases as the effective atomic number of the material increases. If the photon interaction is essentially Compton scattering, the photon energy spectrum will vary from location to location in the material with a variation of counts or flux in the high energy portion of the spectrum. Counts decrease as the electron density increases and vice versa and are mostly independent of the elemental composition of the sample material.

Since there is a unique relationship between electron density and material density for most materials, the gamma radiation flux may be used for measuring material density. Gamma radiation flux decreases in an exponential manner with the increase in material density. Nuclear density gauges according to the subject matter described herein are operable to expose sample material to gamma radiation, determine photon counts of radiation emitted from the sample material and within a predetermined energy level, and determine density of the sample material based upon the photon counts with the predetermined energy level. In practice, both photoelectric absorption and Compton scattering exist with some probability in the entire energy range. Therefore, the energy spectral features (i.e., features in the low energy and high energy portions) can be used to accurately measure the material density.

For a material with an effective atomic number Z and atomic mass A, the electron density $\rho_e$ is provided by the following equation (wherein $\rho$ represents the mass density, and $N_A$ represents Avagadro's number):

$$\rho_e = \rho(Z/A)N_A$$

In general, (Z/A) for a majority of the elements in construction or road paving materials is 0.5. One notable exception is H, where Z/A is about 1. When Z/A is assumed to be 0.5, the density can be determined based upon Compton scattering.

Soils used for construction and asphalt typically have distinctly different elemental composition. For gamma radiation-based density measurements, construction soil material and asphalt material may be treated as different classes of materials because of their different elemental composition. For soil, because of the wide variance in water content, separate measurement of the water content may be used for improving the accuracy of density measurements. In nuclear density gauges, an electromagnetic-based system or a neutron-based system may be used for determining a moisture property of the sample material, such as water content or other moisture content.

When using gamma radiation-based nuclear density gauges for density measurements, the determination of material differences in samples can be challenging. The material that effects gamma radiation propagation is the elemental composition, or the amount of various chemical elements composing the sample material. The density precision demanded by industry can be as high as 0.65%. Therefore, a minor deviation of Z/A from 0.5 may require correction to meet industry density precision requirements.

Table 1 below shows exemplary chemical elements in construction materials and corresponding Z/A.

TABLE 1

Z/A for Exemplary Chemical Elements in Construction Materials

| Element | Z | A | Z/A | % Diff. |
|---------|---|---|-----|---------|
| H  | 1  | 1.00797  | 0.992 | 98.42 |
| C  | 6  | 12.0115  | 0.500 | −0.10 |
| O  | 8  | 15.994   | 0.500 | 0.04  |
| Na | 11 | 22.98977 | 0.478 | −4.31 |
| Mg | 12 | 24.305   | 0.494 | −1.25 |
| Al | 13 | 26.98154 | 0.482 | −3.64 |
| Si | 14 | 28.086   | 0.498 | −0.31 |
| K  | 19 | 39.098   | 0.486 | −2.81 |
| Ca | 20 | 40.08    | 0.499 | −0.20 |
| Ti | 22 | 47.9     | 0.459 | −8.14 |
| Mn | 25 | 54.938   | 0.455 | −8.99 |
| Fe | 26 | 55.847   | 0.466 | −6.89 |

Table 2 below shows exemplary chemical elements for three limestone mixes and three granite mixes used for hot mixed asphalt in the road construction industry. It is notable that most of the limestone aggregates have similar Z/A values, and most of the granite type aggregates have a similar Z/A value. The differences of both values to 0.5 are significant enough to meet industry demand.

TABLE 2

Z and Z/A for Limestone and Granite Aggregate Mixes

| | % Weight Limestone | | | % Weight Granite | | |
|---|---|---|---|---|---|---|
| | 1- | 2- | 3- | 9- | 10- | 11- |
| $SiO_2$ | 0.254 | 0.333 | 0.324 | 0.667 | 0.595 | 0.663 |
| $Al_2O_3$ | 0.0037 | 0.0054 | 0.0034 | 0.136 | 0.156 | 0.138 |

TABLE 2-continued

Z and Z/A for Limestone and Granite Aggregate Mixes

| | % Weight Limestone | | | % Weight Granite | | |
|---|---|---|---|---|---|---|
| | 1- | 2- | 3- | 9- | 10- | 11- |
| CaO | 0.41 | 0.363 | 0.341 | 0.0369 | 0.0642 | 0.0393 |
| Mg | 0.0047 | 0.0053 | 0.032 | 0.0185 | 0.0373 | 0.0195 |
| $Na_2O$ | 0.0006 | 0.0009 | 0.0007 | 0.353 | 0.0403 | 0.0363 |
| $K_2O$ | 0.0008 | 0.0013 | 0.0007 | 0.0291 | 0.01 | 0.0298 |
| $Fe_2O_3$ | 0.0023 | 0.0025 | 0.0027 | 0.0409 | 0.0658 | 0.409 |
| MnO | 0 | 0 | 0 | 0.0008 | 0.001 | 0.001 |
| $TiO_2$ | 0.0007 | 0.289 | 0.0006 | 0.0062 | 0.0086 | 0.0064 |
| $CO_2$ | 0.3232 | 0.2877 | 0.289 | 0.015 | 0.0022 | 0.017 |
| $P_2O_5$ | 0 | 0 | 0.0018 | 0.0016 | 0.0165 | 0.0021 |
| Sum | 1 | 1 | 0.9959 | 0.9873 | 0.9969 | 0.9933 |
| Avg. Z | 10.01 | 10.004 | 9.935 | 10.314 | 10.413 | 10.343 |
| Avg. Z/A | 0.4996 | 0.4995 | 0.4995 | 0.4974 | 0.497 | 0.4973 |

In one embodiment of the subject matter described herein, a Cs-137 gamma radiation source is used in a nuclear density gauge for measuring the density of a sample material. However, other suitable gamma radiation sources with different primary energy levels may be employed, such as a Co-60, Ra-60, or any other suitable isotope gamma radiation source for example. Gamma radiation interacting with a sample material may be measured by an energy-selective, gamma radiation detector, which may be operable to detect gamma radiation in one or more predetermined energy spectrums. For example, an energy-selective scintillation detector may be used, such as a sodium iodide (NaI) crystal mounted on a photomultiplier tube (PMT) for detecting gamma radiation in a predetermined energy spectrum.

As stated above, a nuclear density gauge according to the subject matter described herein may include a moisture property detector for determining a moisture property of a sample material, such as soil. The presence of a significant fraction of water or various other moisture in soil may require correction to manage an anomalous Z/A value of hydrogen. The moisture content of the sample material may be measured using the moisture property gauge and used for correcting density measurements obtained by a nuclear density gauge.

An exemplary moisture property detector is a neutron-based detector, which is sensitive to low energy neutrons from a material. An example is the gas tube detector filled with a gas of He-3 and $CO_2$, known as an He-3 tube. The low energy neutrons have interacted with the hydrogen contained in water in the material. The detector may count the number of slow moving neutrons. The count of slow moving neutrons may correspond with a moisture property of the material. Thus, a moisture property of the material may be determined based on, the neutron count. Neutron-based detectors are calibrated at a construction worksite, because the chemical composition of the soils containing hydrogen, and not associated with water, may affect the measurement results.

Another exemplary moisture property detector is an electromagnetic-based moisture property detector. These detectors and their components include resistance-measuring components, capacitance measuring components, time domain reflectometry components, frequency domain components, antennas, resonators, impedance measuring devices, fringing field devices, and broadband devices, such as monopoles for example. Exemplary techniques for use in determining moisture content include microwave absorption techniques, microwave phase shift techniques, capacitance techniques, volumetric/gravimetric water content techniques, reflection-based techniques, transmission-based techniques, impedance spectroscopy techniques, Gypsum block techniques, resistance techniques, frequency and time domain techniques, and combinations thereof.

An electromagnetic device may measure the permittivity of a material and use the dielectric constant and conductivity to estimate the density of the material. Electromagnetic techniques are sensitive to the chemical composition of the material, because permittivity is a result of molecular bonding, soil chemistry, texture, temperature, water content, void ratio, shape, and history of the material. Fundamentally, the electromagnetic fields respond to the "dipoles per unit volume" or the chemical composition per unit volume. Hence, within even a small area of measurement, there may be significant changes in material properties such as texture, water content, clay content, mineralogy, and gradation. As a result, the electromagnetic device may require frequent calibration.

Nuclear techniques are also a function of chemical composition as a result of photoelectric effects and extraneous hydrogen not associated with water. However, the errors associated with nuclear techniques are very forgiving as compared to dielectric spectroscopy techniques. For neutron water measurements, hydrogen bonding from other chemical compositions is also measured, such as soils that are heavy in mica, salt, iron oxide, etc.

Signals produced by a radiation detector and an electrical property detector may be used by a material property calculation function for calculating a property value associated with a material. The signal produced by the radiation detector may represent an energy level of detected radiation from the material. The signal produced by the electrical property detector may represent a moisture property of the material. The calculated property value may be a density of the material. The calculation of the material property values by the material property calculation function may be implemented by a suitably programmed processor or by any other functionally equivalent device, such as an application specific integrated circuit (ASIC) or a general purpose computer, having suitable hardware, software, and/or firmware components.

Figure 1B:
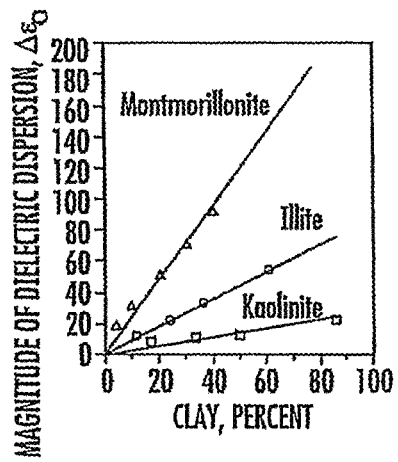
FIG. 1B is a graph of dielectric constant dispersion of several different types of clays.
Figure 1C:
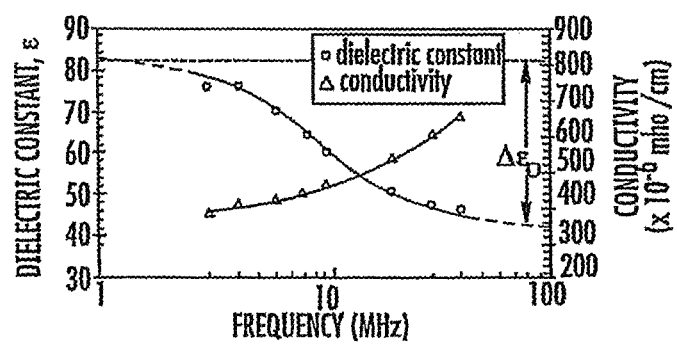
FIG. 1C is a graph of dielectric dispersion of the conductivity and dielectric constant of cohesive soil.

In one example, soil content and losses can be estimated by inspecting dielectric constant dispersion over a microwave bandwidth from DC to a few GHz. FIGS. 1A-1C are graphs illustrating examples of dielectric dispersion for a variety of soils. In particular, FIG. 1A shows a comparison of dielectric constants of clay material (cohesive soil) and non-clay material (non-cohesive soil) over different frequencies. FIG. 1B shows dielectric constant dispersion of several different types of clays. FIG. 1C shows the dielectric dispersion of the conductivity and dielectric constant of cohesive soil.

Information regarding dielectric constant dispersion for known materials may be used in the subject matter described herein for selecting calibration curves for radiation detectors and moisture property detectors. Further, the subject matter described herein may be a combination asphalt and soils gauge having operability to measure asphalt layers in a backscatter mode and soils in a transmission mode. Further, for example, a fringing field planar detector may be attached to a bottom surface of the gauge for simultaneously measuring electromagnetic density and nuclear density. In this mode, the nuclear component can calibrate the electromagnetic detectors in the field for improving the speed of access to a capacitance asphalt density indicator.

The combination of a radiation source/detector and a moisture property detector according to the subject matter described herein may operate in a transmission mode and/or a backscatter mode. The moisture property may be measured using a surface technique, direct transmission, downhole technique, or a technique using a fringing field capacitors, time domain reflectometry (TDR), microwave reflection, microwave transmission, real and imaginary impedance measurements, phase shift, absorption, and spectroscopic analysis. The sensor may be physically integrated into the surface instrument. Alternatively, the sensor may be a stand-alone moisture sensor linked electronically to the surface gauge. An example of a stand-alone system is a moisture sensor integrated into a drill rod. In a use of this exemplary gauge, a drill rod and hammer may be used to punch a hole in the soil to make a pathway for insertion of the source rod.

Nuclear density measurements may be used to obtain bulk density, which may be derived using the following equation (wherein $\rho$ represents bulk density, M represents mass, V represents volume, $M_W$ represents the mass of water, and $M_S$ represents the mass of soil):

$$\rho = M/V = (M_W + M_S)/V$$
$$= (M_W/M_S + M_S/M_S)V/M_S$$

wherein dry density $M_S/V$ is provided by the following equation (wherein $\rho_d$ represents the dry density):

$$\rho_d = \rho/(1+w)$$

Alternatively, a measurement of the volumetric water content may be determined using the following equation (wherein .theta. represents the volumetric water content, V.sub.W represents the volume of water, and V.sub.t represents the total volume):

$$\theta = V_W/V_t$$

The volumetric water content may be converted to pounds per cubic foot (PCF), where it may be subtracted from the wet density moisture measurement provided by the following equation (wherein $\gamma_w$ represents the density of water in proper units):

$$\rho_d = \rho - \gamma_w \theta$$

Variables affecting the electrical response of soils include texture, structure, soluble salts, water content, temperature, density, and frequency. The following equation provides a general relationship for volumetric water content (wherein .di-elect cons. represents permittivity, jA=$-5.3 \times 10^{-2}$, B=$2.92 \times 10^{-2}$, C=$-5.5 \times 10^{-4}$, and D=$4.3 \times 10^{-6}$):

$$\theta = A + B\in + C\in^2 + D\in^3$$

In this equation, permittivity $\in$ is the real part and is a single value measured over the frequency content of the time domain signal. A similar equation may be found using the fringing field capacitor at a single frequency or over an average of frequencies. For results, the moisture detector may be calibrated to the soil type directly from the field.

Figure 2:
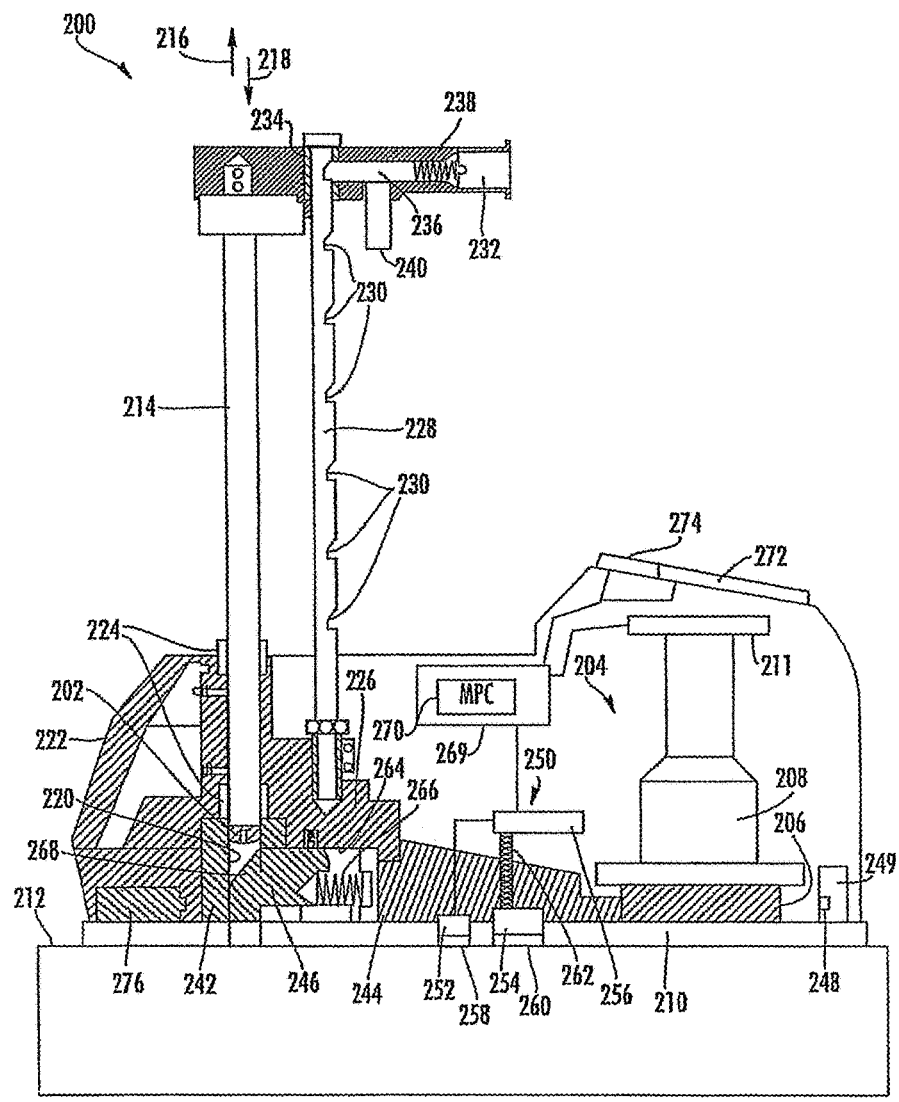
FIG. 2 is a vertical cross-sectional view of a nuclear density gauge for measuring the density of material according to an embodiment of the subject matter described herein.

FIG. 2 is a vertical cross-sectional view of a nuclear density gauge 200 for measuring the density of material according to an embodiment of the subject matter described herein. Gauge 200 may be operable to accurately determine the density of a sample material, such as soil, asphalt, concrete, or any other suitable construction and/or paving material. For example, soil may be measured in a transmission mode, and asphalt may be measured in a backscatter mode. Referring to FIG. 2, gauge 200 may include a primary gamma radiation source 202 and a gamma radiation detector 204. Radiation source 202 may be any suitable radiation source, such as a 300 micro Curie Cs-137 gamma radiation source. Gamma radiation detector 204 may be any suitable type of detector, such as a gamma-ray scintillation detector of the type having a sodium iodide (NaI) crystal 206 mounted on a photomultiplier tube 208. A gamma radiation detector of scintillation-type is an energy selective detector. Radiation detector 204 may be located adjacent to a base plate 210. When gamma radiation strikes NaI crystal 206, photons are released, varying in intensity corresponding to the energy level of the gamma radiation. Photomultiplier tube 208 detects the photons and converts them to electrical signals which, in turn, are communicated to an amplifier for amplifying the electrical signals. Further, the amplified signals may be directed, via an electrical conductor, to a printed circuit board (PCB) 211, where the signals may be processed.

PCB 211 may include suitable hardware (e.g., a multi-channel analyzer (MCA)), software, and/or firmware components for processing the amplified signals 211. PCB may include an analog-to-digital converter for transforming the amplified analog signals into digital signals quantifying the energy level of the gamma radiation (photon) energy. The output of the analog-to-digital converter is directed to an analyzer device operable to accumulate the number of gamma radiation (photon) counts of different energy levels into a plurality of channels, each channel corresponding to a portion of the energy level spectrum. For purposes of density calculation, only a predetermined portion of the overall energy spectrum detected by the detectors is considered. Thus, only the accumulated counts from one or more of the channels corresponding to this predetermined portion are considered for the density calculation. The channel output may be used for density calculations, as described in further detail herein.

Gauge 200 may be adapted to position radiation source 202 in an interior of a sample material 212 to be tested. For example, radiation source 202 may be contained within a distal end of a movable, cylindrical source rod 214, which is adapted to be moved in the vertical directions indicated by arrows 216 and 218. Source rod 214 extends into a vertical cavity 220 in a gauge housing 222. Source rod 214 may be restricted to movement in the vertical directions by guides 224, a support tower 226, and an index rod 228. Guides 224 may include bearings that are operatively positioned to guide source rod 214 through cavity 220 in gauge housing 222. Source rod 214 may be vertically extended and retracted to a plurality of predetermined source rod positions so as to change the spatial relationship between radiation source 202 and detector 204. The plurality of predetermined source rod positions may include a backscatter position and a plurality of transmission positions, wherein radiation source 202 is positioned below base plate 210 of gauge housing 222.

Index rod 228 may be operatively positioned adjacent to source rod 214 for extending and retracting source rod 214. Index rod 228 may include a plurality of notches 230. Each notch 230 corresponds to a predetermined source rod position. For example, one notch may correspond to a "safe" position wherein radiation source 202 is raised and shielded from the sample material. Gauge 200 is shown in the safe position in FIG. 2. The safe position may be used to determine the standard count in a background measurement mode, as described herein. Another notch may correspond to the backscatter mode wherein radiation source 202 is located adjacent to the surface of the sample material underlying gauge 200. Index rod 228 may include a flat side where a resistive depth strip (not shown) may be affixed. Other exemplary depth indicators include Hall effect devices, laser position indicators, and mechanical position indicators.

Source rod 214 may be affixed to a handle 232 for manual vertical movement of source rod 214 by an operator. Index rod 228 extends into a cavity 234 in handle 232. Handle 232 further includes an indexer 236 operatively positioned for engaging notches 230 of index rod 228 in order to temporarily affix source rod 214 in one of the predetermined positions. Indexer 236 is biased into engagement with notches 230. In particular, indexer 236 may be biased into engagement by a spring 238. A trigger 240 allows the operator to move indexer 236 into and out of engagement with notches 230.

Source rod 214 may be positioned in a safe position as shown in FIG. 2 and secured for positioning source 202 within a safety shield 242. When in the safe position, safety shield 242 contains the gamma rays emitted by source 202 minimizes the operator's exposure to radiation. Safety shield 242 may be made of tungsten, lead, or any other suitable radiation shielding material.

Gauge 200 may also include additional shielding for preventing undesirable emission of gamma radiation from gamma radiation source 202. A stationary shield 244, safety shield 242, and a sliding block shield 246 may be included within gauge 200 and positioned for stopping emitted photons from directly reaching detectors of gauge 200. Shields 242 and 246 may be made of tungsten. Alternatively, shields 242, 244, and 246 may be made of any other suitable shielding material. Safety shield 242 may include a hole formed therein and through which rod 214 and source 202 may pass. In the safe position, source 202 may be positioned in the interior of safety shield 242 for preventing photons of source 202 from reaching the detectors of gauge 200. Stationary shield 244 may be positioned for preventing photons from reaching the detectors through pathways through the interior of gauge 200.

Detector 204 may be energy-calibrated by use of another gamma radiation source 248. Radiation source 248 may be positioned within an aluminum support 249 and positioned adjacent to base plate 210 and detector 204. In one example, radiation source 248 may be a 1 to 2 micro Curie Cs-137 gamma radiation source. Radiation source 248 may be used to energy calibrate detector 204 for managing environmental effects, such as temperature. In one example, radiation source 248 may produce main energy peaks of about 33 and 662 kilo electronvolts (keV). The energy peaks produced by radiation source 248 may be used for calibrating detector 204 for use as a multi-channel spectrum analyzer, as described in further detail herein. In an alternative embodiment, a small leak hole may be provided in cylindrical shield 242 to allow the energy from gamma radiation source 202 to radiate towards detector 204 for energy-calibrating detector 204.

Further, gauge 200 may include a moisture property detector 250 operable to determine a moisture property of sample material 212. In particular, detector 250 may measure the permittivity of sample material 212 and use the dielectric constant and conductivity to estimate the moisture property of sample material 212. The following exemplary moisture properties, alone or combinations thereof, may be detected by a moisture property detector for use in determining the density of a sample material: permittivity, resistivity, dielectric constant, conductivity, permeability, dispersive properties, change in dielectric constant with frequency, change in conductivity with frequency, the real part of permittivity (i.e., dielectric constant), the imaginary part of permittivity, and combinations thereof.

In this example, moisture property detector 250 may include a moisture signal source 252, a moisture signal detector 254, and a PCB 256. Moisture property detector 250, as an electromagnetic detector, may operate in a far field radiation mode, a near field mode, a passive fringing mode, or by coupling the fields from source to receiver through sample material 212. Signal source 252 may generate an electromagnetic field and be positioned near a surface of sample material 212 such that the electromagnetic field extends into sample material 212. Alternatively, signal source 252 and/or detector 254 may be positioned within an interior of sample material 212 via source rod 214. In one embodiment, a combination source/detector device may be attached to a source rod for obtaining depth information. In another embodiment, a combination source/detector device may be external to the gauge and detached.

Moisture signal detector 254 may detect at least a portion of the electromagnetic field from sample material 212 that was produced by source 252. A frequency and/or time domain technique may be used for determining a moisture property. The electromagnetic field may range from direct current (DC) to microwave. Exemplary techniques for use in determining a moisture property include using fringing field capacitors to produce an electromagnetic field; time domain reflectometry techniques; single-frequency moisture techniques; sweeping-frequency moisture techniques; microwave absorption techniques; and microwave phase shift techniques. Further, suitable moisture signal detectors include detectors operable to measure the real and imaginary parts of a dielectric constant at a single frequency, multiple frequencies, continuous sweeps of frequencies, and/or chirps of frequency content. In the time domain, direct steps or pulses may be produced by a signal source and detected by a detector for determining a moisture property. In one example, source rod 214 may be pulsed, the response received at detector 254, and the phase velocity calculated from the time-distance information. Further, a fast Fourier transform (FFT) technique may be applied to the frequency and time domains for determining a moisture property. The conductivity and permittivity of sample material b may be determined based on the detected electromagnetic field.

Gauge 200 may include a source window 258 and a receiver window 260 associated with signal source 252 and detector 254, respectively. Source window 258 and receiver window 260 may extend through base plate 210 such that electromagnetic fields may pass through base plate 210 and between signal source 252 and detector 254. Exemplary window materials include aluminum oxide, sapphire, ceramics, plastics, and suitable insulators.

PCB 256 may be in operable communication with signal source 252 and detector 254. PCB 256 may include suitable hardware, software, and/or firmware components for control of signal source 252 and detector 254. In particular, PCB 256 may control signal source 252 to generate an electromagnetic field. For example, PCB 256 may supply power to circuitry of signal source 252 for generating a predetermined electromagnetic field. Further, PCB 256 may be operable to receive a signal from detector 254 representing detected electromagnetic fields via a coaxial cable 262. Based on the signal representation, PCB 256 may determine a moisture property of sample material 212. For example, measurement of the magnitude and phase of reflected signals may provide an impedance that is a function of constitutive parameters permittivity and permeability of the material. An impedance bridge may be used for obtaining the complex impedance at lower frequencies. For higher frequencies, reflectometers incorporating mixers or detectors (e.g., magnitude and phase integrated circuits, manufactured by Analog Devices, Inc. of Norwood, Mass.) may be used. For time domain reflectometry (TDR), diode techniques and timing/recording circuitry may be used to obtain voltage as a function of time.

Other exemplary techniques for determining a moisture measurement include measuring a DC resistivity, surface impedance methods, propagation techniques, wave tilt, self-impedance, probe impedance, mutual impedance, transient electromagnetic methods, laboratory resistivity methods, capacitance methods, transmission line methods, waveguide methods, free space methods, and mm wave and microwave remote sensing.

Moisture measurement may rely on single variable or multi-variable equations. For example, water may be detected using one variable such as the relative dielectric constant $\in_r$. Interfacial polarization is an important property response for heterogeneous materials. Further, the relaxation frequency of some soils is on the order of 27 MHz. At lower frequencies, the measured dielectric constant has the effects of the Maxwell Wagner phenomenon leading to errors in the water measurement that are also a function of temperature. Other exemplary variables include conductivity, permittivity, and the disperson of the change in conductivity and the change in permittivity with frequency. Further, for example, the relaxation frequency of some soils is on the order of 27 MHz.

In one example, the capacitance of a fringing field detector is measured using a feedback loop in an oscillator circuit. The frequency is provided by the following equation (wherein $C_{eff}$ represents the effective capacitance including the surrounding medium, parasitics in the circuitry, and nominal capacitances in the tank circuit, and L represents the inductance):

$$2\pi F = 1/(\mathrm{sqrt}(LC_{eff}))$$

The ratio between a reference frequency and the frequency with the fringing field capacitor switched may be calibrated against moisture. The sensitivity of the measurement at these frequencies due to salt concentrations should be considered. The end result is that chemical composition errors must be corrected, leading to many different calibration curves for the soil types. Further, discussion is provided in U.S. Pat. Nos. 4,924,173; and 5,260,666, each of which are incorporated herein by reference in their entireties.

Microwave-based moisture property detectors may be advantageous, for example, because such detectors can perform density-independent moisture measurements. Such detectors may be advantageous over neutron-based moisture property detectors, because neutron-based detectors are density dependent. Further, it is desirable to reduce the use of neutron sources because of NRC regulations and fees associated with neutron sources.

Density-independent moisture measurements may be made based on a two-parameter measurement of attenuation (or magnitude) and phase shift in a transmission- or reflection-type mode. Alternatively, density-independent moisture measurements may be made using microwaves at a single frequency. A two-parameter method may be implemented by comparing the real and imaginary parts of the dielectric constant, as shown in the following equation (wherein E represents the dielectric constant):

$$\in = \in(\omega)' - j\in(\omega)''$$

A density independent calibration factor $A(\psi)$ (wherein $\psi$ is the wet-based volumetric water content) may be used for canceling density components. The principle of density-independent moisture measurements is based on both the real and imaginary part of the dielectric constant being related to dry material and water constituents, which change as a function of density. Density components may be empirically canceled by combining $\in(\rho_d, \psi)'$ and $j\in(\rho_d, \psi)''$ in the following equation:

$$A(\Psi) = \frac{\varepsilon(\rho_d, \psi)' - 1}{\varepsilon(\rho_d, \psi)''}$$

The above equation assumes that $\in(\omega)'$ and $E(\omega)''$ are linearly independent functions of $\rho_d$ and $\psi$.

The loss tangent $\in'/\in''$ may describe the material interaction and response. The behavior of the complex permittivity implies that normalizing both $E(\omega)'$ and $j\in(\omega)''$ with density may reduce density effects. Further, data pairs may be normalized with bulk density as functions of temperature and moisture content. The following equation provides a measure of bulk density without prior knowledge of moisture content or temperature given that moisture density relationships are independent (wherein $a_f$ represents slope, k represents intercept, $a_f$ is related to the frequency, and k related to the dry dielectric):

$$\in''/\rho = a_r(\in'/\rho - k)$$

Alternatively, the following equation provides a measure of bulk density:

$$P = (a_f \in' - \in'')/ka_f$$

At high frequencies, water is the dominant factor associated with energy loss related to $\in''$ in the material, and the energy storage is related to $\in'$. Thus, a density-independent function for water content is based on the loss tangent $\in''/\in'$. Therefore, again, by normalizing the loss tangent by the density provided by the above equation results in the following equation:

$$\xi = \in''/(\in'(a_f \in' - \in''))$$

Here, the constant $ka_f$ is omitted, and the loss tangent has been normalized, resulting in a moisture function with reduced density effects. Experimentally, for granular materials, it has been found that .xi. is linear with moisture content $ka_f$ is a function of the measurement frequency and remains constant for data pairs of $\in'$ and $\in'$ when they have been normalized by density.

Based on experimental results, it can be shown that, as temperature increases, the bound water becomes easier to rotate and the dielectric constant increases. Thus, for the water measurement, temperature correction may be necessary.

Since $\xi$ is a function of moisture content with the density effects removed, and since it is experimentally found to be linearly related to moisture, calibration as a function of moisture and temperature can be implemented by fitting to the following linear equation:

$$\sqrt{\xi} = A*M + B(T)$$

In this equation, the intercept B increases with temperature, but the slope A is constant. For granular materials, the following equation was empirically derived (wherein temperature is measured in Celsius):

$$B(T) = 9.77 \times 10^{-4} *T + 0.206$$

The moisture content may then be determined using the following equation:

$$\% M = (\sqrt{\xi}(a_f\in',\in'') - B(T))/A$$

In one embodiment, samples of soil may be extracted from the field and fit to this equation as a function of moisture yielding the constants A and B at a particular temperature. Generic curves may also be defined whereby a field offset is performed in use. Therefore, any moisture property detector operable to measure the real and/or imaginary portions of the dielectric constant of a material at a single frequency, multiple frequencies, or continuous sweeps of frequencies, chirps of frequency content, on the surface or down-hole can be incorporated into embodiments of the subject matter described herein.

Microwaves are more sensitive to free water than bound water but are also a function of the constituents of the chemical makeup of the dry mass and water mass mixture. However, a dry mass and water mass mixture is less susceptible to ionic motion and DC conductivity when considering the following equation:

$$\in = \in(\omega)' - j\in(\omega)'' = \in(\omega)' - j(\in(\omega)_d'' + \sigma_{d,c}/\omega\in_0$$

The higher frequencies reduce the effects of DC conductivity and measure more of the dielectric permittivity. However, soil specific calibrations may be necessary. The differences in the calibrations are much smaller than their low frequency counterparts. Thus, if the material changes slightly without a gauge operator's knowledge, suitable results may still be obtained. Therefore, the microwave electromagnetic techniques have soil specific calibrations or offsets that may be required when comparing sandy foams to clay classes of soils.

Sliding block shield 246 is configured to be slidable within a chamber 264 and associated with a spring 266, which is adapted for biasing shield 246 in a direction towards an interior of safety shield 242. In the safe position, at least a portion of shield 246 is positioned in the interior of safety shield 242 for preventing photons emitted by source 202 from passing through safety shield 242. On movement or rod 214 in the direction indicated by arrow 218 towards the position for transmission mode, block shield 246 is pushed by an end of rod 214 away from the interior of safety shield b and against the biasing direction of spring 266. Shield 246 may include a beveled portion 268 adapted to engage an end of rod 214 for pushing shield 246 away from the interior of safety shield 242 such that rod 214 and source 202 may move into the position for the transmission mode. Movement of shield 246 away from the interior of safety shield 242 compresses spring 266.

Figure 3:
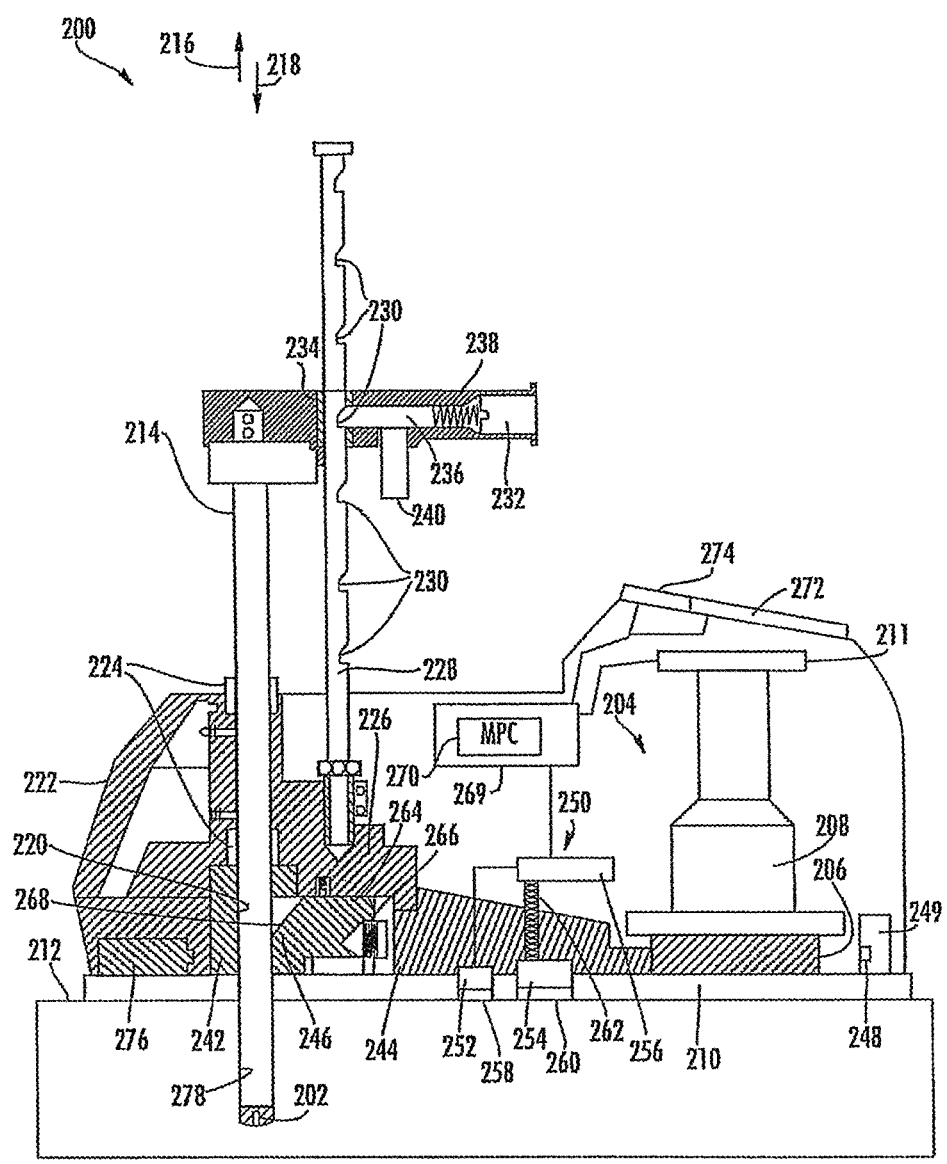
FIG. 3 is a vertical cross-sectional view of the nuclear density gauge shown in FIG. 2 configured in a transmission mode for measuring the density of a sample material according to an embodiment of the subject matter described herein.

FIG. 3 is a vertical cross-sectional view of nuclear density gauge 200 configured in a transmission mode for measuring the density of sample material 212 according to an embodiment of the subject matter described herein. Referring to FIG. 3, in the transmission mode, radiation source 202 may be positioned in an interior of sample material 212 for emitting radiation from the interior of sample material 212. In the transmission mode, radiation source 202 may emit radiation through sample material 212 for detection by radiation detector 204. Further, PCB 211 may produce a signal representing an energy level of the detected radiation. Moisture property detector 250 may determine a moisture property of sample material 212 and produce a signal representing the moisture property. A PCB 269 may include a material property calculation function (MPC) 270 configured to calculate a property value associated with sample material 212 based upon the signals produced by radiation detector 204 and moisture property detector 250.

MPC 270 may include suitable hardware, software, and/or firmware components for implementing density measurement and calibration procedures according to the subject matter described herein. MPC 270 may include one or more processors and memory components. Exemplary MPC components include one or more of pre-amplifiers, spectroscopic grade Gaussian amplifiers, peak detectors, and analog-to-digital converters (ADCs) for performing the processes described herein. Procedure status, feedback, and density measurement information may be presented to an operator via one or more interfaces of gauge 200.

A nuclear density gauge may be calibrated for density and moisture measurements. In one embodiment, measurements of the dielectric constants of different synthetic materials are fit to a calibration curve. The materials may be selected to represent materials found in the construction field. Solid metal blocks of known properties may be used for calibrating a nuclear density gauge. Exemplary metal blocks for use in calibration include a magnesium (Mg) block (MG), a Mg and aluminum (Al)-laminated block (MA), an Al block (AL), and a Mg and polyethylene-laminated block (MP). The MG, MA, and AL set may be used for density calibration. The MG and MP set may be used for moisture calibration. It is noted that the gravimetric density of Mg is about 110 pounds per cubic foot (PCF), Al is about 165 PCF, and MG and Al are about 135 PCF.

For density measurements, when calibrating a nuclear density gauge for soil measurements, typical soils are assumed to have a Z/A of 0.5. To emulate Z/A=0.5, the gravimetric density values of the calibration blocks $\rho_{grav}$ may be normalized with respect to the Z/A value and used with gamma radiation counts to determine calibration coefficients. A calibration model is provided by the following equation (wherein CR is the count ratio for the test sample, $\rho_{norm}$ is the normalized density of the test sample, and A, B, and C are calibration coefficients):

$$CR = A \times e^{-B\rho_{norm}} - C$$

Soil normalization constants are shown in Table 3 below.

TABLE 3

| Soil Normalization Constants | | | |
|---|---|---|---|
| Block | MG | MA | AL |
| Normalization Constants | 0.988 | 0.974 | 0.964 |

When calibrating a nuclear density gauge for asphalt measurements, the normalized gravimetric density values are used. Asphalt normalization constants are shown in Table 4 below.

TABLE 4

| Asphalt Normalization Constants | | | |
|---|---|---|---|
| Block | MG | MA | AL |
| Normalization Constants | 0.988 | 0.989 | 0.949 |

A direct gauge reading on a test material is relative to the Z/A value used in the calibrations. For materials having significantly different Z/A values, the gauge may be calibrated specifically for the material.

For moisture example of laboratory calibration, a soil sample may be removed from a field site. The soil sample is dried in an oven according to ASTM standard 2216. Different amounts of water are added to the dried soil, and the material is stored for a predetermined time period. The soils are then compressed into a coaxial cylinder. Next, a function of the water content and measurements of the permittivity are obtained as a function of frequency over a broad band. The permittivity is recorded as a function of frequency and temperature. The coaxial cylinders are then weighed and dried to obtain the actual water and density content. For single frequency measurements, the permittivity may be normalized with density and corrected for temperature. The slope of may be found using the equations described above. Further, by using the equations described herein, the moisture equation may be derived and programmed into the nuclear gauge for field use.

In field use, the calibration for specific materials is performed by finding an offset to the gauge by comparing gauge readings to density values as determined by a conventional method. For example, a sand cone technique (ASTM standard D-1556) may be used for soils. In another example, an operator may use the gauge to perform a measurement in the field, and use an oven test according to the ASTM standard 2216 to evaporate the water and obtain the moisture content in volumetric or gravimetric units. The resulting value in this example may be used to offset factory or laboratory calibration. In an example for asphalt, a coring and water displacement technique (ASTM standard D-2726) may be used.

In field calibrations, the nuclear density gauge may be positioned on the soil. Typically, the soil is wet with different moisture contents. Measurements of the real part of the dielectric constant may be obtained as a function of the water content. The response is fit to a linear equation, such as y=mx+b, wherein x is the response of the gauge. The nuclear density gauge may be calibrated in steps similar to the steps used for laboratory calibration, except for one or more of the following, only the imaginary portion of the dielectric constant is used, only the capacitance of a detector is used, only the resistance measurement is used, only TDR is used, only frequency response is used, only the relative dielectric constant is used, and only dispersion data is used.

As stated above, the presence of a significant fraction of water or various other moisture in construction-type soil may require correction to manage an anomalous Z/A value of hydrogen. The wet density of soil is provided by the following equation (wherein WD represents the wet density of soil, GD represents the gauge density (mass per unit volume) from direct calibration, and M represents gauge moisture content (mass of water per unit volume of moist soil)):

$$WD = GD - (1/20)M$$

These corrections to direct nuclear gauge readings improve the accuracy of the density estimate provided Compton scattering is the only interaction mechanism for gamma radiation. Detected gamma radiation of energies greater than 0.15 MeV meets this requirement for typical construction materials.

Gas ionization detectors, such as Geiger Mueller detectors, may be used in nuclear density gauges for gamma radiation or photon counting. Such detectors have relatively higher detection efficiencies in the 0 to 0.2 MeV range than in the 0.2 MeV or higher range but cannot accurately detect the color or energy of counted photons. The photon counts recorded by such detectors also contain the attenuation effect of low energy gamma radiation from photoelectric absorption. The model described above for handling the Z/A effect may not be met. As a result, density accuracy may be compromised.

A scintillation detector is an energy-selective detector operable to selectively use gamma radiation energies above 0.15 MeV during gauge calibration and measurement. The signal amplitude of a sodium iodide crystal/PMT detector depends linearly on the detected photon energy. A histogram of the number of detected photons versus energy signal amplitude provides a gamma radiation spectrum. For a given photon energy, the energy signal amplitude depends on the PMT signal gain and the environmental temperature. Therefore, with no feedback control of the detector, the position of key features of the spectrum (i.e., spectrum peaks) vary with time. When counts in a particular energy window (or range) are required, spectrum stabilization techniques may be used to minimize the effects form short-term signal amplitude variability, as described in further detail herein.

Figure 4:
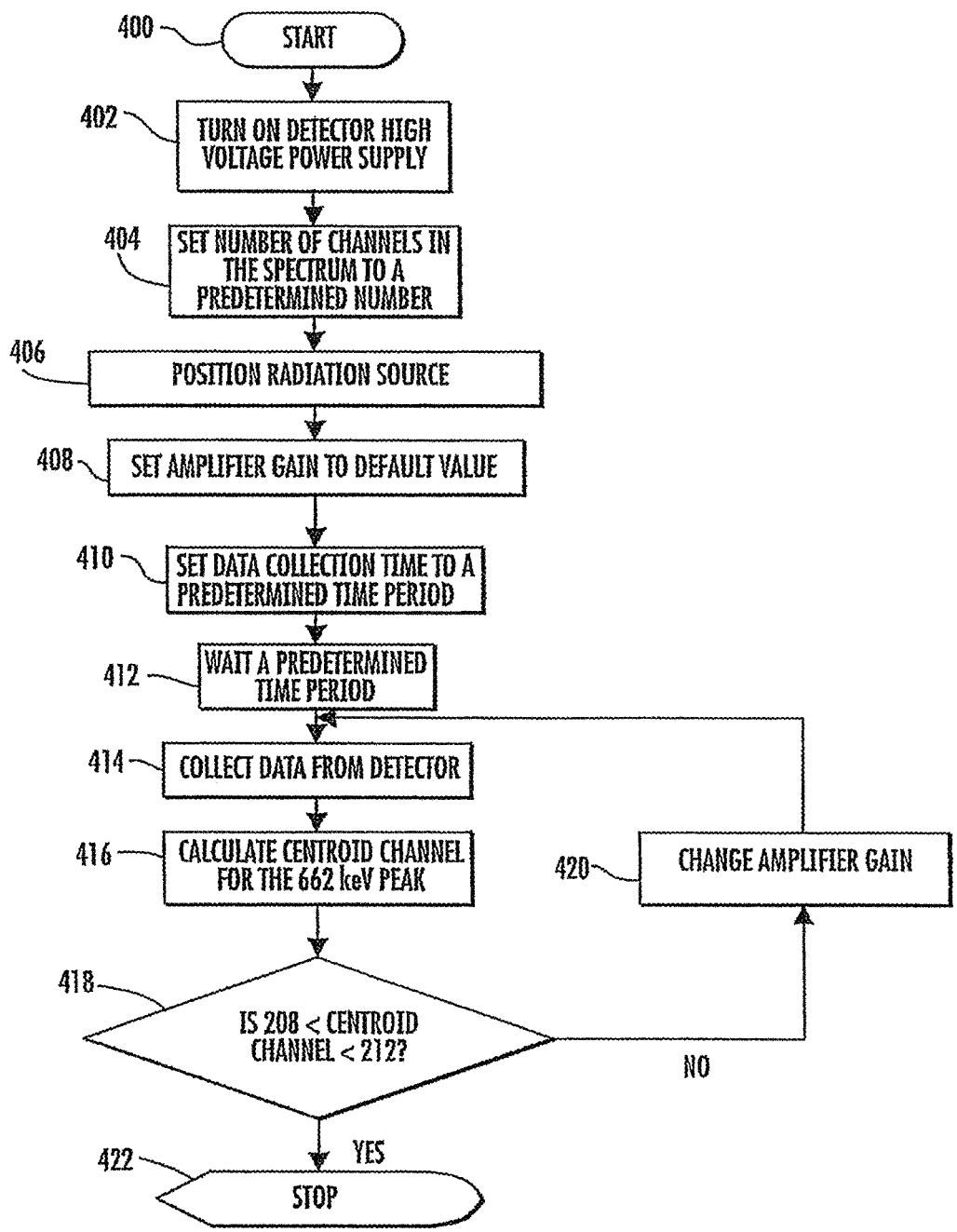
FIG. 4 is a flow chart of an exemplary process by which the gauge shown in FIGS. 2 and 3 may be initialized according to an embodiment of the subject matter described herein.

FIG. 4 is a flow chart illustrating an exemplary process by which gauge 200 shown in FIGS. 2 and 3 may be initialized at the beginning of a workday according to an embodiment of the subject matter described herein. In this example, radiation detector 204 is calibrated for use as a multichannel spectrum analyzer. Referring to FIG. 4, the process starts at block 400. In block 402, a high voltage power supply that is connected to radiation detector 204 is turned on. For example, gauge 200 may include a battery 276 configured to supply power to radiation detector 204. In block 404, a predetermined number of channels in the energy spectrum of the radiation provided by radiation source 202 to detector 204 may be set. In this example, the number of channels in the spectrum is set to 512. In block 406, radiation source 202 is positioned for emitting radiation. Radiation detector 204 may detect radiation emitted by radiation source 202. As stated above, radiation source 202 may be Cs-137 gamma radiation source for producing energy peaks of about 33 and 662 keV. The energy peaks produced by radiation source 202 may be used for calibrating detector 204. During calibration, source rod 214 may be positioned in a safety mode such that radiation detector 204 is shielded from radiation source 202.

In block 408, an amplifier gain of radiation detector 204 is set to a default value. Further, in block 410, a data collection time of radiation detector 204 is set to a predetermined time period (e.g., 20 seconds). In block 412, the process waits a predetermined time period (e.g., between about two and five minutes). After detector 204 has warmed up, a radiation count is obtained from the underlying material.

Next, in blocks 414-420, an amplifier gain of radiation detector 204 may be adjusted until a centroid channel is between 208 and 212. The amplifier gain may be set such that the centroid of the 662 keV gamma radiation peak from Cs-137 is in the middle of the 208 to 222 channel window. As the gauge is used, depending on the environment, the centroid may move in the acceptance window defined by channels 200 and 220. Prior use for measurements, MPC 207 may verify that the centroid lies in this channel window. If MPC 207 determines that the centroid lies outside this channel window, the centroid may be moved back to the mid area of the channel window defined by channels 208 and 212 in about 20 seconds, and a message may be displayed on a display screen 274 of gauge 200 indicating the delay. In a typical use, the gain may need to be moved to center the peak approximately one or two times per day. During idle times, MPC 207 may implement an active routine for changing gain.

In particular, in block 414, data is collected from radiation detector 204. For example, radiation detector 204 may communicate acquired data and communicate the data to MPC 270. MPC 270 may calculate the centroid channel for the 662 keV energy peak (block 416). In block 418, it is determined whether the centroid channel is between 208 and 212. If it is determined that the centroid channel is not between 208 and 212, the amplifier gain is changed (block 420). Otherwise, if it is determined that the centroid channel is between 208 and 212 the process stops at block 422. Now, radiation detector 204 is ready for measurements.

The centroid may move in the acceptance window during normal temperature conditions in the field. Further, when the gauge is used on hot asphalt, the increase in temperature of the radiation detector can result in a centroid location being outside of the acceptance window. If the centroid location is found to be outside of the acceptance window, the system gain may be adjusted to center the centroid at channel 210. The system gain may be changed by adjusting either the gain of the shaping amplifier or the voltage supplied to the photomultiplier tube of the radiation detector.

Figure 5:
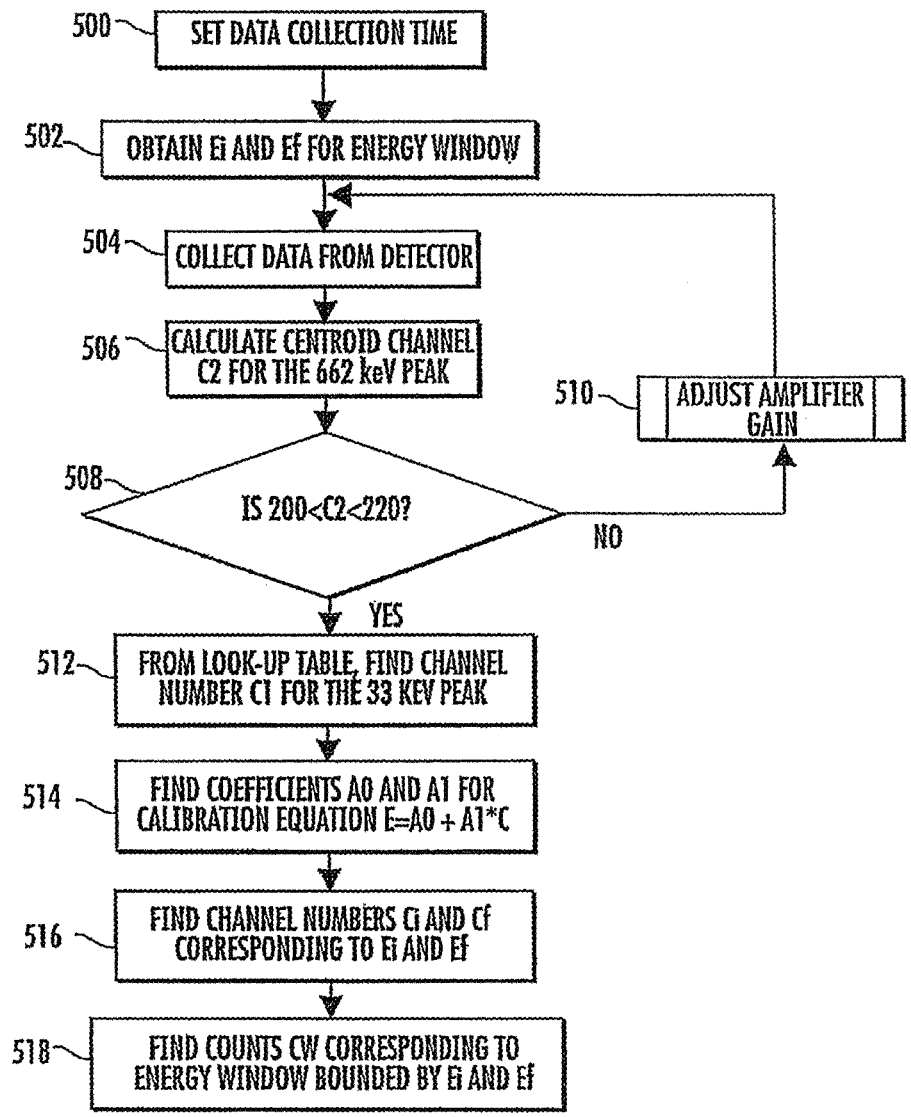
FIG. 5 is a flow chart of an exemplary process for determining detector counts within an energy window according to an embodiment of the subject matter described herein.

A detected energy level is analyzed when the location of a predetermined energy level peak is within an acceptance window. For example, an energy level peak of 662 keV must be within an acceptance window of between channels 200 and 220 within a 512 channel spectrum. FIG. 5 is a flow chart of an exemplary process for determining detector counts within an energy window defined by energy values Ei and Ef according to an embodiment of the subject matter described herein. The process of FIG. 5 may be implemented after the gauge has been initialized, for example, by the exemplary process of FIG. 4. Referring to FIG. 5, in block 500, a data collection time of radiation detector is set to a predetermined time period (e.g., 15 or 30 seconds). Next, in block 502, energy values Ei and Ef are obtained. In block 504, data is collected from radiation detector 204.

Next, in block 506, MPC 270 may calculate a centroid channel C2 for the 662 keV energy peak. MPC 270 may determine whether the centroid channel C2 is between channels 200 and 220 (block 508). If the centroid channel C2 is not between channels 200 and 220, the process can adjust the amplifier gain of radiation detector 204 according to a process similar to that described with respect to blocks 414-420 of FIG. 4 (block 510). Otherwise, if the centroid channel C2 is not between channels 200 and 220, the process proceeds to block 512.

In block 512, using a look-up table, a centroid channel C1 may be found for the energy level peak of 33 keV. Next, in block 514, MPC 270 may solve for coefficients A0 and A1 for calibration equation E=A0+A1*C, a first order energy calibration where C is the channel number. In block 516, MPC 270 may solve for channel numbers Ci and Cf corresponding to energy values Ei and Ef, respectively. MPC 270 may then find counts CW corresponding to energy values Ei and Ef (block 518). CW is the total counts of channels Ci to Cf, where a count value is associated with each channel. Counts CW may be used for density calculation processes, as described in detail herein. Since channel numbers are integer values, fractional channel numbers may be handled in a manner as an analog-to-digital converter digitizes signals.

Typically, sample material contains natural radioactivity, such as natural radio isotopes of K, U, and Th. When using a low activity gamma radiation source, the natural radioactivity manifests itself as noise. Since the signal-to-noise ratio is low and the magnitude of the noise varies from material to material, a separate measurement of the noise (background) is required for maintaining the accuracy of the measurement. Nuclear gauge 200 is shown in FIG. 2 configured in a background measurement mode for managing noise. As stated above, in this configuration, shields 242, 244, and 246 prevent gamma radiation produced by radiation source 202 from reaching radiation detector 204. The gamma radiation reaching radiation detector 204 is produced by material sample 212 (natural radioactivity or background) and stabilization source 248. Since the small stabilization source 248 is positioned near radiation detector 204, the background spectrum can be measured with adequate accuracy. Background counts are not necessary for 8 milli Curie Geiger-Mueller detector-based instruments, because the signal-to-noise ratio is high.

Figure 6:
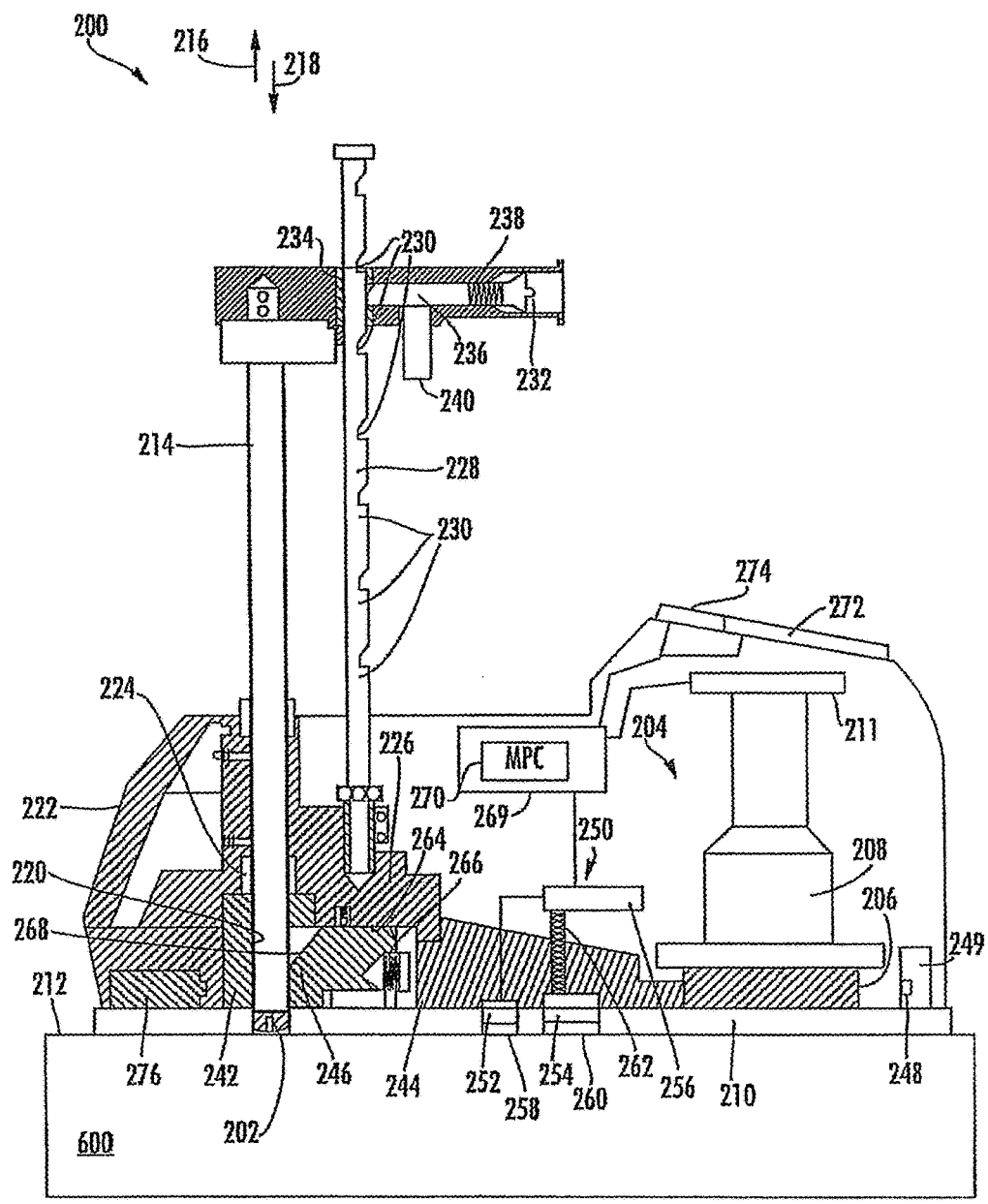
FIG. 6 is a vertical cross-sectional view of the nuclear density gauge shown in FIGS. 2 and 3 for measuring the density of asphalt layers according to an embodiment of the subject matter described herein.

Nuclear density gauge 200 is operable in a backscatter mode for measuring asphalt layers. FIG. 6 is a vertical cross-sectional view of nuclear density gauge 200 for measuring the density of asphalt layers according to an embodiment of the subject matter described herein. In the backscatter mode, source rod 214 is positioned such that radiation source 202 is on a surface of an asphalt layer 600.

Components of a nuclear density gauge operable in a backscatter mode were used for demonstrating the functionality of its use as a transmission gauge. The gauge components were positioned on a magnesium/aluminum (Mg/Al) standard calibration block of size 24"×17"×14". The gauge components included a 300 micro Curie Cs-137 gamma radiation source fixed on a source plate. The base of the gauge included a gamma radiation detector having a NaI crystal mounted on a photomultiplier tube. PC-based electronics were used for data acquisition.

Further, a source plate was attached to a 0.25-inch thick 14"×14" aluminum mounting bracket having an open slot with screw hole positions. The aluminum plate was attached to the 17"×14" side of each metal calibration block. The source plate was also attached to the aluminum plate so that the source is 2", 4", 6", 8", 10", and 12" below the top surface (a 24"×17" surface) of the calibration block. Each radiation source position is called an operating mode.

Standard metal calibration blocks made of Mg, Mg/Al, and Al were used for calibrating the gauge. A standard count was used to compensate for the decrease of the gamma radiation count over time due to radioactive decay and other variations. In this experiment, counts for the gauge operating in the backscatter mode and placed on the Mg block was used as the standard count.

For gauge calibration, data was collected for each of the operating modes, wherein the radiation source is positioned at 2", 4", 6", 8", 10", and 12" below the top surface of the calibration block. A four minute count time was selected for the calibration of the six operating modes. The net counts in the energy range from 150 to 800 keV were used. Further, radiation spectra were taken on the Mg block, the Mg/Al block, and the Al block without the radiation source for obtaining gamma radiation background.

Figure 7:
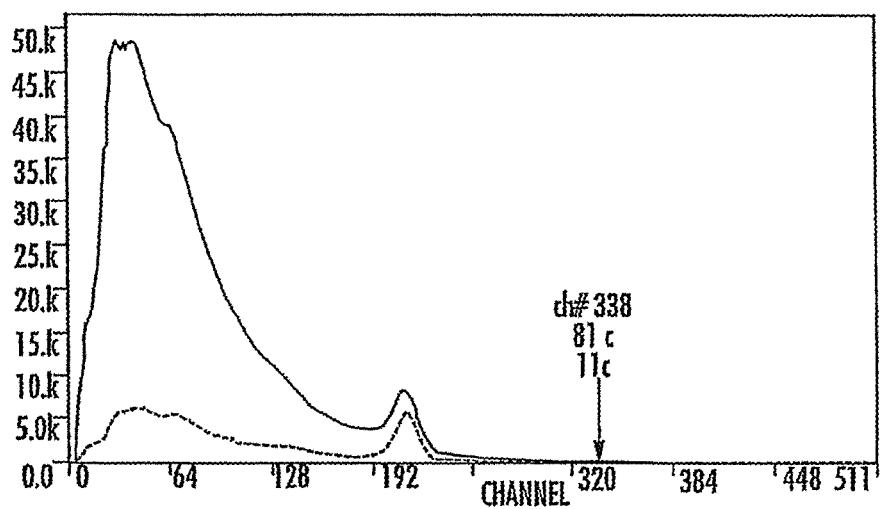
FIG. 7 is a graph of experimentation results showing gamma radiation spectra for a standard count.
Figure 8:
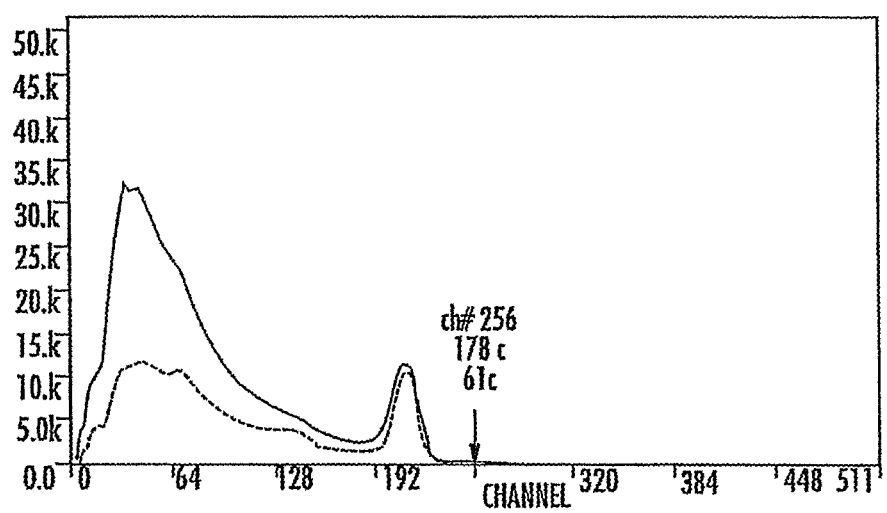
FIG. 8 is a graph of experimentation results showing gamma radiation spectra for a 4-inch operating mode.

In backscatter mode experiments, the radiation source was positioned about 2" from the radiation detector and about 7" from the radiation detector. It is noted that, in actual use, the radiation source and the radiation detector are in a fixed position with respect to one another. For each operating mode position, the transmission mode was tested with the radiation source near the detector in the Mg block, the Mg/Al block, and the Al block. For obtaining the standard count, the gauge was configured in the backscatter mode with and without the gamma radiation source being positioned on the Mg block. FIGS. 7 and 8 are graphs of experimentation results showing gamma radiation spectra for the standard count and the 4-inch operating mode, respectively.

In one embodiment, the mathematical model used for calibrating a nuclear density gauge is provided by the following equation (wherein, CR represents the count ratio, and A, B, and C represent calibration constants):

$$CR = A * \exp(-B * Density) - C$$

CR is defined as the ratio of the net counts for a mode on a block of density p to the net standard count. For example, for a 6" transmission mode on a Mg/Al block, the net count is the difference of the counts for the gauge with the gamma radiation source on the block and the gauge without the gamma radiation source on the block. The net standard count is the difference of the counts for the gauge in the backscatter mode on the Mg/Al block with the gamma radiation source and without the gamma radiation source. Table 5 below shows the calibration constants for the six operating modes.

TABLE 5

Calibration Constants

| Mode | A | B | C |
|---|---|---|---|
| 2-inch | 2.046 | 0.024546 | −0.02849 |
| 4-inch | 1.503 | 0.20331 | 0.00624 |
| 6-inch | 1.533 | 0.022028 | 0.009511 |
| 8-inch | 1.799 | 0.026834 | 0.003163 |
| 10-inch | 2.1219 | 0.032571 | −1.29E−06 |
| 12-inch | 1.4854 | 0.033686 | 0.000386 |

Tables 6 and 7 below show the density precision obtained based on the calibration data for 20-second and 1-minute counts, respectively.

TABLE 6

Density Precision for a 20-Second Count

| | Mg | | Mg/Al | | Al | |
|---|---|---|---|---|---|---|
| Mode | Density | 1-sigma | Density | 1-sigma | Density | 1-sigma |
| 2-inch | 109.4 | 0.21 | 133.5 | 0.36 | 162.6 | 0.69 |
| 4-inch | 109.4 | 0.23 | 133.5 | 0.34 | 162.6 | 0.58 |
| 6-inch | 109.4 | 0.25 | 133.5 | 0.38 | 162.6 | 0.68 |
| 8-inch | 109.4 | 0.27 | 133.5 | 0.48 | 162.6 | 0.97 |
| 10-inch | 109.4 | 0.33 | 133.5 | 0.66 | 162.6 | 1.67 |
| 12-inch | 109.4 | 0.47 | 133.5 | 1.03 | 162.6 | 2.66 |

TABLE 7

Density for a 1-Minute Count

| | Mg | | Mg/Al | | Al | |
|---|---|---|---|---|---|---|
| Mode | Density | 1-sigma | Density | 1-sigma | Density | 1-sigma |
| 2-inch | 109.4 | 0.13 | 133.5 | 0.21 | 162.6 | 0.4 |
| 4-inch | 109.4 | 0.13 | 133.5 | 0.19 | 162.6 | 0.31 |
| 6-inch | 109.4 | 0.13 | 133.5 | 0.2 | 162.6 | 0.36 |
| 8-inch | 109.4 | 0.15 | 133.5 | 0.26 | 162.6 | 0.55 |
| 10-inch | 109.4 | 0.18 | 133.5 | 0.38 | 162.6 | 0.96 |
| 12-inch | 109.4 | 0.28 | 133.5 | 0.63 | 162.6 | 1.66 |

Figure 9:
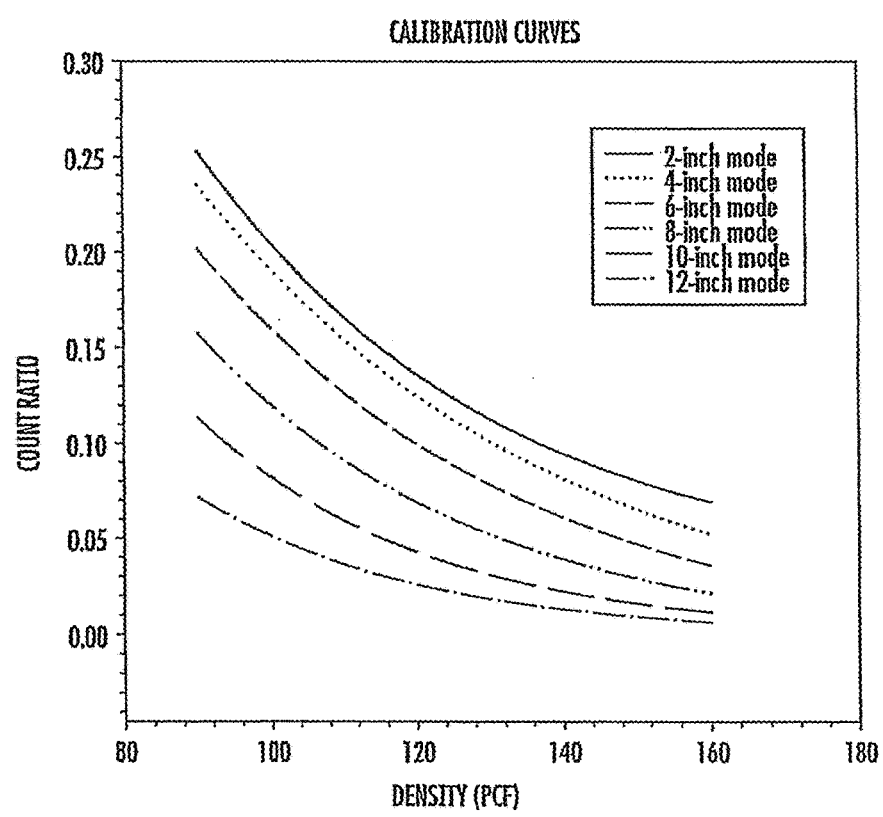
FIG. 9 is a graph showing calibration curves for density measurements.

FIG. 9 illustrates a graph showing calibration curves for density measurements.

In one example of gauge 200 being used in the transmission mode, counts in the energy interval from 150 to 800 keV for all spectra are used for density calculation. In this example, count are normalized per 1-minute. For a 4-inch operating mode on an Mg block, the net count for Mg is 341084. The net standard count is 2181382. Further, solving from the equation CR=A*Exp(-B*Density)-C, density is provided by the following equation:

$$Density = (-1/B) * Ln((Cr+C)/A)$$

The calibration constants A, B, and C for the 4-inch mode may be used from Table 5 above, which may be stored in a memory associated with MPG 270. CR is provided by net count/standard count, which is 341084/2181482 in this example. By using the above equation, MPC 270 may determine that the density is 109.4 PCF.

A nuclear density gauge according to the subject matter described herein may operate in a backscatter mode for quality control and quality assurance testing of asphalt pavements. Since asphalt pavements are typically built with multiple layers including different mixes and thicknesses, an accurate estimate of the density requires consideration of the chemical composition, surface roughness, and the thickness of the test layer.

Thickness of the top layer of an asphalt pavement may be specific for the road construction project. For thin asphalt layers, a density reading of the top layer may depend on the material type and density of other asphalt layers below the top layer. The gauge reading may be corrected if the bottom layer density is known accurately by using features observed for layer-on-layer measurements. This correction method is referred to a nomograph method and described in the Troxler Electronic Laboratories, Inc. manual for the Model 3440 surface moisture density gauge, produced by Troxler Electronic Laboratories, Inc., of Research Triangle Park, N.C., the content of which is incorporated herein by reference in its entirety. The Troxler Electronic Laboratories, Inc. Model 4640 density gauge is another exemplary gauge for thin-layer measurements, which uses two detector systems and the features observed for layer-on-layer measurements.

When a photon is Compton scattered by an electron, the energy of the photon depends upon the scattering angle. When a gamma radiation source and detector are placed on a planar semi-infinite medium, the single scattered photons for a given thickness have predetermined energies. Such energy windows may be determined experimentally using measurements of known thickness layers of materials, such as layers of glass on an Mg/Al calibration block. The following energy bands may be used to measure layers with thicknesses between 0.75" and 2.5":

240 to 400 keV: 0.75" to 1.25"
220 to 400 keV: 1.25" to 1.75"
200 to 400 keV: 1.75" to 2.0"
180 to 400 keV: 2.0" to 2.5".

Figure 10:
FIG. 10 is a graph of density measurements for various gamma-ray energy bands as a glass thickness was varied.

A dual layer structure made with dissimilar materials was formed in the laboratory by placing glass slabs on an Mg/Al standard size block. Next, gamma-ray spectra were acquired by placing a nuclear density gauge on glass. FIG. 10 illustrates a graph of density measurements for various gamma-ray energy bands as the glass thickness varied. The upper energy of all bands was 400 keV. By using the energy band 80 to 400 keV, the gauge measured a depth of about 3 inches. By using another energy band from about 240 to 400 keV, the gauge measured a depth of about 1 inch.

Figure 11:
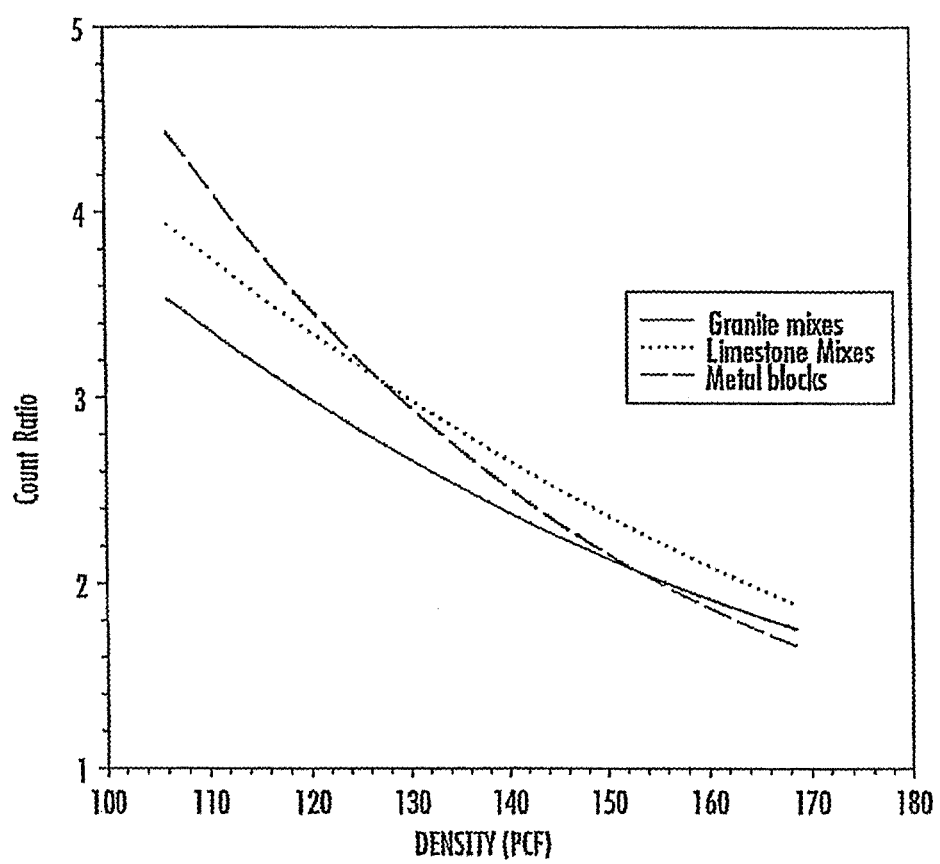
FIG. 11 is a graph of the calibration curves for granite and limestone mixes as determined from experimentation.

When reading the density of thick layers, the window counts for density determination contain gamma radiation of low energies. Such gamma radiation is also absorbed by the photoelectric process to thereby cause an error in density. The two major classes of aggregate types, granite and limestone, have two different normalization constants for gamma radiation in the Compton scattering region and varying degrees of photoelectric absorption. As a result, the granite and limestone aggregate types have distinct calibration curves. FIG. 11 illustrates a graph of the calibration curves for granite and limestone mixes as determined from experimentation. A prior identification of aggregate type can improve the estimation of the density.

MPC 270 may use the gamma radiation spectrum for identifying aggregate types. The photoelectric absorption process results in reduced low-energy gamma radiation flux for materials with high atomic numbers than that for materials with low atomic numbers. The average atomic number of limestone mixes is higher than that for granite mixes. Therefore, low energy counts in the spectrum normalized to density can be used for aggregate type identification. For example, CL can represent the counts in a low-energy window with low and high energy limits ($EI_l$ and $EI_h$), and CH can represent the counts in a high-energy window with low and high energy limits ($EH_l$ and $EH_h$). The ratio of Rc=CL/CH may be used for aggregate identification. Based on experiments, it was found that Rc<R0 for limestone mixes and that Rc>R0 for granite mixes.

In the asphalt industry, the asphalt volume for density determination may be defined in various ways. The material volume of the asphalt may be determined by excluding surface texture. Further, a water displacement technique and its variations may be used for density measurements. Using gamma radiation techniques for density measurements defines the asphalt volume including surface roughness. Therefore, direct gamma radiation density values are lower than that measured by water displacement techniques. Further, the air void content of asphaltic materials (V) has a strong correlation to the surface roughness. If the density difference between the water displacement and gamma radiation techniques is dρ, an empirical relationship between dρ and V may be found using the following equations:

$$d\rho = B0_g + B1_g * V + B2_g * V^2 \text{ for granite, and}$$

$$d\rho = B0_l + B1_l * V + B22_l * V^2 \text{ for limestone.}$$

Figure 12:
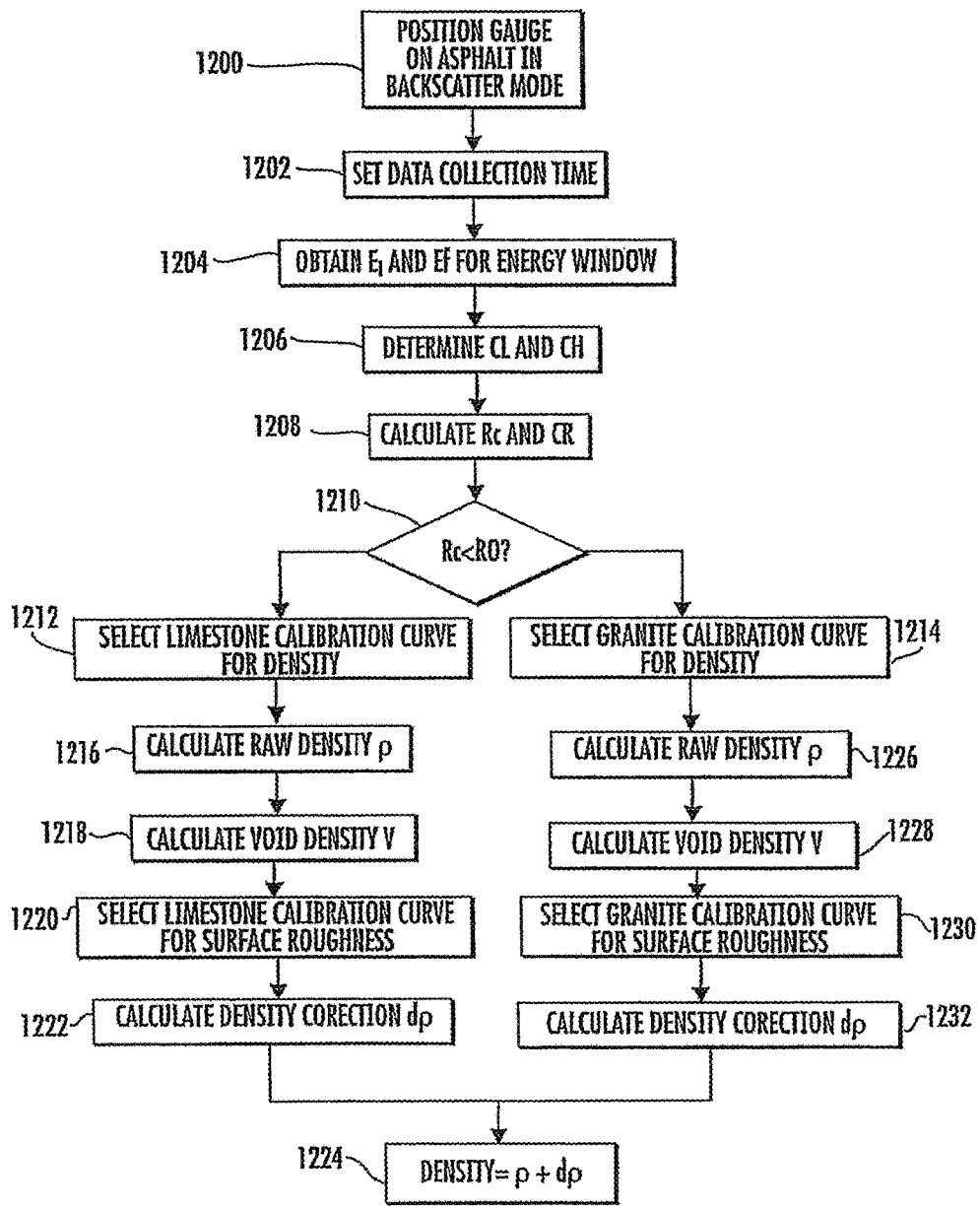
FIG. 12 is a flow chart of an exemplary process for density measurements in a backscatter mode using the gauge shown in FIG. 6 according to an embodiment of the subject matter described herein.

Asphalt density measurements may be determined using gauge 200 configured in the backscatter mode shown in FIG. 6. FIG. 12 is a flow chart illustrating an exemplary process for density measurements in a backscatter mode using gauge 200 according to an embodiment of the subject matter described herein. Referring to FIG. 12, in block 1200, gauge 200 is positioned on a top surface of asphalt layer 600 as shown in FIG. 6. Further, source rod 214 is positioned in the backscatter mode such that radiation source 202 is positioned near the top surface of asphalt layer 600. Further, in the backscatter mode, sliding block shield 246 is moved in the backscatter mode such that radiation source 202 can emit radiation towards and into asphalt layer 600. An operator may interface with gauge 200 to initialize a density measurement process in a backscatter mode for implementation by MPC 270.

In block 1202, a data collection time of radiation detector is set to a predetermined time period (e.g., between 15 and 30 seconds). Next, in block 1204, energy values Ei and Ef for the energy window are obtained. The detector counts may be communicated to MPC 270 for use in determining density of asphalt layer 600 in a backscatter mode.

In block 1206, steps similar to the steps described with respect to block 504-518 may be implemented for determining low window counts CL and high window counts CH. As stated above, CL can represent the counts in a low-energy window with low and high energy limits ($EL_l$ and $EL_h$), and CH can represent the counts in a high-energy window with low and high energy limits ($EH_l$ and $EH_h$).

In block 1208, MPC 270 may determine Rc ratio and count ratio CR. The ratio of Rc=CL/OH may be used for aggregate identification. The ratio CR=CH/Standard Count may be used for density determination.

In block 1210, MPC 270 may determine whether Rc is less than R0. As stated above, Rc<R0 for limestone mixes, and that Rc>R0 for granite mixes. If it is determined that Rc is less than R0, a limestone calibration curve is selected (block 1212). Otherwise, if it is determined that Rc is not less than R0, a granite calibration curve is selected (block 1214).

In block 1216, MPC 270 may determine raw density ρ using the limestone calibration curve. Further, in block 1218, MPC 270 may determine void content V. MPC 270 may also select a limestone calibration curve for surface roughness (block 1220). In block 1222, MPC 270 may calculate a density correction dρ. In one example, d.ρ may be determined by using one of the above equations showing the empirical relationship between d.ρ and V. In block 1224, MPC 270 may determine the density of asphalt layer 600 by adding raw density ρ and density correction dρ.

In block 1226, MPC 270 may determine raw density ρ using the granite calibration curve. Further, in block 1228, MPC 270 may determine void content V. MPC 270 may also select a granite calibration curve for surface roughness (block 1230). In block 1232, MPC 270 may calculate a density correction dρ. In block 1224, MPC 270 may determine the density of asphalt layer 600 by adding raw density ρ and density correction dρ.

Soil density measurements may be determined in a similar manner to the asphalt density measurements. Some soils may have minerals having high atomic number elements, such as K and Fe. According to one embodiment, an energy-selective detector may be used for identifying soil type based on features in the low-energy part of the spectrum. By using a predetermined calibration for the identified soil type, density errors may be reduced or avoided. Further, a correction to the gamma radiation-based density measurement may be made based on a determined moisture density. Soil density measurements may be determined using gauge 200 configured in the transmission mode shown in FIG. 3.

Figure 13:
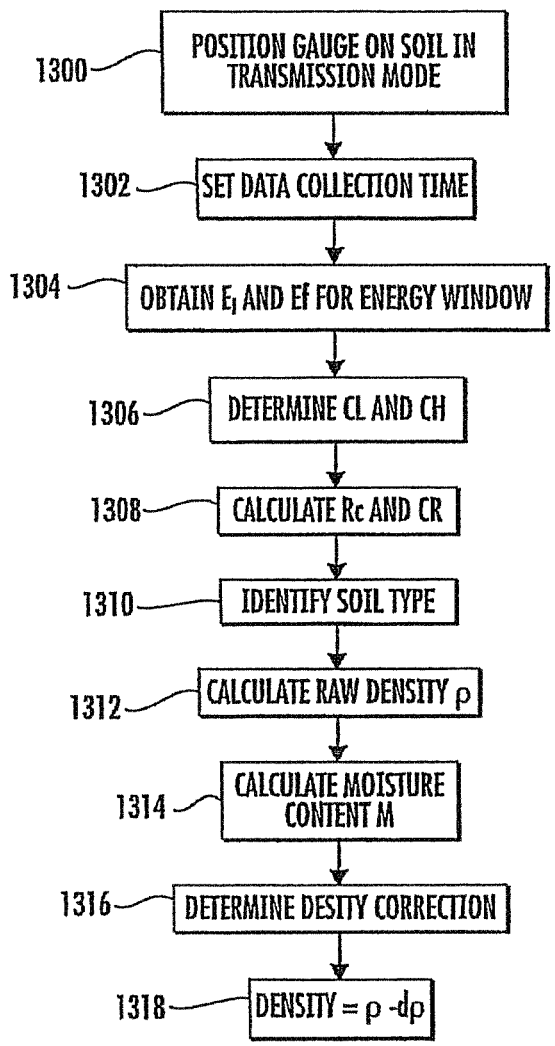
FIG. 13 is a flow chart of an exemplary process for density measurements in a transmission mode using the gauge shown in FIG. 3 according to an embodiment of the subject matter described herein.

FIG. 13 is a flow chart illustrating an exemplary process for density measurements in a transmission mode using gauge 200 shown in FIG. 3 according to an embodiment of the subject matter described herein. Referring to FIG. 13, in block 1300, gauge 200 is positioned as shown in FIG. 3 on a top surface of sample material 212, which is soil in this example. Further, source rod 214 is positioned in a transmission mode such that radiation source 202 is positioned in the interior of soil 212 within a vertical access hole 278 formed in soil 212. In the transmission mode, gamma radiation emitted by radiation source 202 can directly transverse through soil 212 to radiation detector 204. An operator may interface with gauge 200 to initialize a density measurement process in a transmission mode for implementation by MPC 270.

In block 1302, a data collection time of radiation detector is set to a predetermined time period (e.g., between 15 and 30 seconds). Next, in block 1304, energy values $E_l$ and $E_h$ for the energy window are obtained. The detector counts may be communicated to MPC 270 for use in determining density of soil 212 in a transmission mode.

In block 1306, steps similar to the steps described with respect to block 504-518 may be implemented for determining low window counts CL and high window counts CH. As stated above, CL can represent the counts in a low-energy window with low and high energy limits ($EL_l$ and $EL_h$), and CH can represent the counts in a high-energy window with low and high energy limits ($EH_l$ and $EH_h$).

In block 1308, MPC 270 may determine Rc ratio and count ratio CR. The ratio of Rc=CL/CH may be used for aggregate identification. The ratio of CR=CH/Standard Count may be used for density determinations.

In block 1310, MPC 270 may identify a soil type of soil 212 based on the value of Rc.

Based on the identified soil type, a raw density p of soil 212 may be determined using a calibration curve corresponding to the identified soil type (block 1312). MPC 270 may be operable to determine the raw density p using the calibration curve. The calibration curves for various soil types may be generated based on calibration block calibrations. As stated above, exemplary calibration blocks include Mg, Mg/Al, and Al.

Next, in block 1314, a moisture content M of soil 212 may be determined using moisture property detector 250. Moisture content may be determined using a neutron-based technique or an electromagnetic-based technique.

In block 1316, MPC 270 may determine density correction dρ. Density correction d.rho. may equal the moisture content M/20. In block 1318, MPC 270 may determine the density of soil 212 by subtracting density correction dρ from the raw density ρ.

The calculated density value may be displayed to an operator via display screen 274. In one embodiment, the density calculation are carried out repeatedly at frequency intervals as measurements are made, such as every one to two seconds. Instead of waiting until the end of a 2 to 4 minute count to display the density value, this approach makes it possible to provide to the operator an almost real-time display of the calculated density value while the count is still proceeding. The density values may be displayed to the operator graphically as a function of time. As the density value settles to a steady state, the operator may decide to accept the calculated density value as being sufficiently accurate, and to discontinue the measurement procedure. The radiation source/detector and moisture property detector components may be positioned in any suitable position in the interior or the exterior of a gauge. For example, a moisture signal source may be positioned in an end of a source rod for generating an electromagnetic field from within an interior of a sample material. In this example, a moisture signal detector may be positioned within a gauge housing for detecting the electromagnetic field transmitted through the sample material and generating a signal representing the detected electromagnetic field. Further, the generated electromagnetic field may be an electromagnetic pulse or step. In another example, a moisture signal source and detector may be attached to a drill rod operable to penetrate a sample material for positioning the moisture signal source in the interior of the sample material. In this example, the moisture signal detector may generate a signal representative of detected electromagnetic fields, and communicate the signal via a wired or wireless communication connection to an MPC in a gauge housing.

A moisture property detector according to the subject matter described herein may include one or more of several electromagnetic-based components. For example, the moisture property detector may include a duroid patch antenna configured to detect an electromagnetic field generated by an electromagnetic field source. The resonance frequency or input impedance may be monitored as a function of a dielectric constant.

In another example, a moisture property detector may include a cavity-backed dipole antenna. The antenna may include a dipole operable at predetermined frequency (e.g., 2.45 GHz). Further, the antenna may include a metallic cavity filled with a dielectric material to decrease the overall size of the component. The cavity may function as an energy focus based upon the geometry of the cavity surface.

In another example, a moisture property detector may include a monopole. The monopole may detect broadband DC to microwave electromagnetic fields. In use, the monopole may be driven by an oscillator. The impedance may be measured as a function of frequency and various soil parameters obtained. Alternatively, the impulse response can be obtained and convolution and transform theory by be applied for obtaining soil properties. Further, the monopole may be coated by an insulator to reduce the energy loss in the soil.

In yet another example, a moisture property detector may include a suitable fringing field, low-frequency device. The device may include a signal line, a ground, and one or more conductors.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed:

1. A material property gauge for determining a property of a material, the material property gauge comprising:
    at least two electrodes configured to be inserted or driven into the surface of the soil material;
    a moisture property gauge electrically connected to the at least two electrodes and configured to use the at least two electrodes to generate an electromagnetic field within the soil material to determine a permittivity response of the soil material for generating a measure of moisture of the soil material at a predetermined depth;
    a nuclear gauge comprising a radiation source configured to be positioned into or on the surface of the soil, the nuclear gauge being configured to determine a wet density of the soil material when in operation and the radiation source is positioned into or on the soil surface; and
    at least one processor and memory configured to:
        determine a dry density of the soil material based on the measure of moisture and the wet density of the soil material,
        wherein the at least two electrodes are positioned at the predetermined depth.

2. The material property gauge of claim 1, wherein the moisture property gauge is configured to use the at least two electrodes to generate the electromagnetic field in a frequency domain.

3. The material property gauge of claim 2, wherein the at least two electrodes are operable to measure an impedance.

4. The material property gauge of claim 1, wherein the moisture property gauge is configured to produce a signal representing one of a single frequency, multi-frequency, sweeps of frequency, and time-modulated frequency sweeps for obtaining frequency response of the soil material.

5. The material property gauge of claim 1, wherein the at least two electrodes are operative in a range that encompasses from DC to a microwave region.

6. The material property gauge of claim 1, wherein the at least two electrodes comprise a microwave sensor operable in a mode of one of absorption, reflection, transmission, resonance, amplitude, and phase measurement techniques.

7. The material property gauge of claim 1, wherein the at least two electrodes are operable to measure one or more of real and imaginary parts of a permittivity related response, dispersive effects related to at least one of multiple frequencies, a time modulated frequency, and continuous sweeps of frequencies, or impedance response at one of a single frequency, multiple frequencies, continuous sweeps of frequencies, time modulated frequency, and chirps of frequency content in association with a moisture value.

8. The material property gauge of claim 1, wherein the nuclear gauge comprises a detector that is one of a solid state sensor, a scintillation sensor, an energy selective detector, a counting tube, and a Geiger Mueller sensor.

9. The material property gauge of claim 1, wherein the moisture property gauge is configured to generate the electromagnetic field in a time domain.

10. The material property gauge of claim 1, wherein the moisture property gauge is configured to generate the electromagnetic field for penetrating the soil material in the form of one of a step, a pulse, a frequency, a time modulated frequency, or a time waveform, and
wherein the moisture property gauge further comprises a sensor configured to measure the reflection or transmission response of the step, pulse, frequency, time modulated frequency, or time waveform from the soil material in the form of the response to the step, pulse, frequency, time modulated frequency, or time waveform of the material to the electromagnetic field.

11. The material property gauge of claim 10, wherein the at least one processor and memory are configured to determine the amplitude and phase or timing of the response based on an impedance measurement including the effects of at least the complex permittivity, dispersive effects, conductivity, resistivity, reactance, susceptance, and dielectric properties of the soil material.

12. The material property gauge of claim 1, wherein the moisture property gauge comprises at least one of a time domain reflectometry (TDR) type sensor and a frequency domain sensor.

13. The material property gauge of claim 12, wherein the moisture property gauge is configured to analyze the electromagnetic time response based on a transient electromagnetic technique and optionally encompass a dispersive property of the soil material.

14. The material property gauge of claim 1, wherein the at least one processor and memory are configured to:
determine water content of the soil material based on the measure of moisture; and
determine the dry density of the soil material by removing the determined water content from the determined wet density of the soil material.

15. The material property gauge of claim 1, wherein the at least one processor and memory are configured to correct the measure of moisture and density for at least one of temperature, and chemical properties related to Hydrogen within the soil material.

16. The material property gauge of claim 1, wherein the moisture property gauge is configured to use measurements in a frequency or a time domain comprising at least one or combinations of mixers, amplitude and phase detecting components, bridges, reflectometers, diode techniques, timing and recording circuitry, resistivity, near field techniques, far field techniques, fringing techniques, and coupling from source to receiver techniques.

17. The material property gauge of claim 1, further comprising the material property gauge configured to determine material properties of at least one of asphalt, pavement, stone, sub-base material, sub-grade material, cement, agricultural soils, batch plant materials, water-cement materials, alkali-silica reactions, various soils, flexible asphalt, and any combination thereof,
wherein the material properties relate to a concrete curing rate, a concrete chloride inclusion, a sodium chloride content, a concrete delamination, and a water content.

18. The material property gauge of claim 1, wherein the moisture property gauge is communicatively linked to the material property gauge wirelessly.

19. The material property gauge of claim 1, wherein the moisture property gauge is integrated into and communicates directly with a material property gauge processor.

20. The material property gauge of claim 1, wherein the at least two electrodes are operable to measure one or more of real and imaginary parts of a permittivity related response related to a change in frequency comprising at least one of a spectroscopic analysis, an impedance spectroscopy, a dispersion, a change of dielectric constant, and a change of conductivity.

21. The material property gauge of claim 1, wherein the at least one processor and memory is configured to further correct for a density prior to determining the dry density from the wet density.

22. A method of determining a property of a material, the method comprising:
inserting at least two electrodes into a soil material, wherein the at least two electrodes are positioned at a predetermined depth of the soil material;
using the at least two electrodes to generate an electromagnetic field within the soil material to determine a permittivity response of the soil material for generating a measure of moisture of the soil material;
positioning a radiation source into or on the surface of the soil;
determining a wet density of the soil material based on detection of radiation from the radiation source while the radiation source is in or on the surface of the soil; and
determining a dry density of the soil material based on the measure of moisture content and the wet density of the soil material.

23. The method of claim 22, wherein using the at least two electrodes comprises using the at least two electrodes to generate the electromagnetic field in a frequency domain.

24. The method of claim 22, further comprising using the at least two electrodes to measure at least one impedance effect such as that of resistivity, conductivity, reactance, susceptance, dispersive properties, and capacitance associated with permittivity of the soil.

25. The method of claim 22, further comprising using the moisture property gauge to produce a signal representing one of a single frequency, multi-frequency, sweeps of frequency, and time-modulated frequency sweeps for obtaining frequency response of the soil material.

26. The method of claim 22, wherein the at least two electrodes are operative from in a range that encompasses DC to a microwave region.

27. The method of claim 22, wherein the at least two electrodes are a microwave sensor operable in a mode of one of absorption, reflection, transmission, resonance, amplitude, and phase techniques.

28. The method of claim 22, further comprising using the at least two electrodes to measure one or more of real and imaginary parts of a permittivity, dispersive effects related to at least one of multiple frequencies, a time modulated frequency, or continuous sweeps of frequencies, or impedance response at one of a single frequency, multiple frequencies, continuous sweeps of frequencies, time modulated frequency, and chirps of frequency content in association with a moisture value.

29. The method of claim 22, wherein the nuclear gauge comprises a detector that is one of a solid state sensor, a scintillation sensor, an energy selective detector, a counting tube, and a Geiger Mueller sensor.

30. The method of claim 22, further comprising using the moisture property gauge to generate the electromagnetic field in one of a time domain and a frequency domain.

31. The method of claim 30, wherein the amplitude and phase or timing of the response is determined by the complex permittivity, conductivity, resistivity, dispersive, and dielectric properties of the soil material.

32. The method of claim 22, further comprising using the moisture property gauge to generate the electromagnetic field for penetrating the soil material adjacent the two or more electrodes in the form of one of a step, a pulse, a frequency, a time modulated frequency, or a time waveform, and
wherein the method further comprises using a sensor to measure the reflection or transmission response of the step, pulse, frequency, time modulated frequency, or time waveform from the soil material in the form of the response to the step, pulse, frequency, time modulated frequency, or time waveform of the material to the electromagnetic field.

33. The method of claim 22, wherein the moisture property gauge comprises at least one of a time domain reflectometry (TDR) and a frequency domain reflectometry (FDR) type sensor.

34. The method of claim 33, further comprising using the moisture property gauge to analyze the electromagnetic time or frequency response based on a transient electromagnetic technique and optionally encompass a dispersive property of the soil material.

35. The method of claim 22, further comprising: determining water content of the soil material based on the measure of moisture; and determining the dry density of the soil material by removing the determined water content from the determined wet density of the soil material.

36. The method of claim 22, wherein the moisture measurement is determined using a moisture property gauge configured to use techniques in a frequency or a time domain comprising at least one or combinations of mixers, amplitude and phase measuring components, bridges, reflectometers, diode techniques, timing and recording techniques, resistance, near field techniques, far field techniques, fringing techniques, and coupling from source to receiver techniques.

37. The method of claim 36, wherein the moisture property gauge is communicatively linked to a material property gauge wirelessly.

38. The method of claim 37, wherein the moisture property gauge is integrated into and communicates directly with a material property gauge computer.

39. The method of claim 22, wherein the at least two electrodes are operable to measure one or more of real and imaginary parts of a permittivity related response comprising a spectroscopic analysis, an impedance spectroscopy, a dispersion, a change of dielectric constant, and a change of conductivity, based on the generated electromagnetic field and a response of the soil material to the generated electromagnetic field.

40. The method of claim 22, further comprising further correcting the moisture measurement for density prior to determining the dry density from the wet density.

41. A method of determining a property of a material, the method comprising:
inserting at least two electrodes into a soil material to a predetermined depth;
using the at least two electrodes to generate an electromagnetic field within the soil material to determine a permittivity response of the soil material for generating a measure of moisture of the soil material;
positioning a radiation source into or on the surface of the soil;
determining a wet density of the soil material based on detection of radiation from the radiation source while the radiation source is in or on the surface of the soil; and
determining a dry density of the soil material based on the measure of moisture content and the wet density of the soil material.

42. The method of claim 41, further comprising determining characteristics of a pavement material such as moisture content, mineralogy, clay content, sand content, concrete curing properties, and texture related properties via dispersion techniques, relaxation phenomenon, spectroscopy techniques, impedance spectroscopy techniques, and temperature correction techniques.

43. The method of claim 42, further comprising calculating a corrected density of the soil material based on the determined characteristics.

44. The method of claim 42, further comprising operating a moisture property detector in a far field radiation mode, a near field mode, a fringing mode, or by coupling the fields from source to receiver through a sample material.

45. The method of claim 44, further comprising determining the property of the material based on the material's permittivity, resistivity, dielectric constant, conductivity, permeability, reactance, susceptance, dispersive properties, change in dielectric constant with frequency, change in conductivity with frequency, the real part of permittivity, the imaginary part of permittivity, or combinations thereof via measurements of the material obtained from the moisture property detector.

* * * * *